US012741081B2

(12) United States Patent
Koops et al.

(10) Patent No.: US 12,741,081 B2
(45) Date of Patent: Sep. 22, 2026

(54) INFUSION SET, SYSTEM COMPRISING SUCH AN INFUSION SET, AND USE OF SUCH A SYSTEM

(71) Applicant: INREDA DIABETIC B.V., Goor (NL)

(72) Inventors: Robin Koops, Goor (NL); Mickael Gilbert Robert Boulay, Goor (NL)

(73) Assignee: INREDA DIABETIC B.V., Goor (NL)

(*) Notice: Subject to any disclaimer, the term of this patent is extended or adjusted under 35 U.S.C. 154(b) by 463 days.

(21) Appl. No.: 18/285,837

(22) PCT Filed: Apr. 5, 2022

(86) PCT No.: PCT/EP2022/059017
§ 371 (c)(1),
(2) Date: Oct. 5, 2023

(87) PCT Pub. No.: WO2022/214489
PCT Pub. Date: Oct. 13, 2022

(65) Prior Publication Data

US 2024/0197982 A1 Jun. 20, 2024

(30) Foreign Application Priority Data

Apr. 7, 2021 (NL) ..................................... 2027930

(51) Int. Cl.
*A61M 5/14* (2006.01)
*A61M 39/10* (2006.01)

(52) U.S. Cl.
CPC ........ *A61M 5/1407* (2013.01); *A61M 5/1413* (2013.01); *A61M 2039/1077* (2013.01); *A61M 2205/14* (2013.01); *A61M 2205/6027* (2013.01)

(58) Field of Classification Search
CPC .............. A61M 5/1407; A61M 5/1413; A61M 2039/1077; A61M 2205/14; A61M 2205/6027; A61M 39/10
See application file for complete search history.

(56) References Cited

U.S. PATENT DOCUMENTS

2008/0243085 A1 10/2008 DeStefano
2016/0235910 A1* 8/2016 Damiano ............ A61M 5/1452
2021/0030949 A1* 2/2021 Damiano ............ A61M 39/105
2021/0283328 A1* 9/2021 Damiano ............ A61M 5/1723

FOREIGN PATENT DOCUMENTS

WO 2015061690 A1 4/2015

OTHER PUBLICATIONS

International Search Report and Written Opinion for the International Application No. PCT/EP2022/059017, mailed Jul. 15, 2022, 8 pages.

* cited by examiner

*Primary Examiner* — Phutthiwat Wongwian
*Assistant Examiner* — Rene D Ford
(74) *Attorney, Agent, or Firm* — KDW Firm PLLC

(57) ABSTRACT

An infusion set for a system for regulating the concentration of glucose in the blood of a person includes an infusion element having an infusion means for infusing a substance into a body of said person, and a transport element having a transport means for transporting the substance. The infusion element is adjustable from a neutral condition to at least a first or second condition, and in the first or second condition the infusion element is adapted to a first or second type of transport element only. A system for regulating the concentration of glucose in the blood of a person including two such infusion sets and to the use of such a system.

16 Claims, 11 Drawing Sheets

Figure 1A:
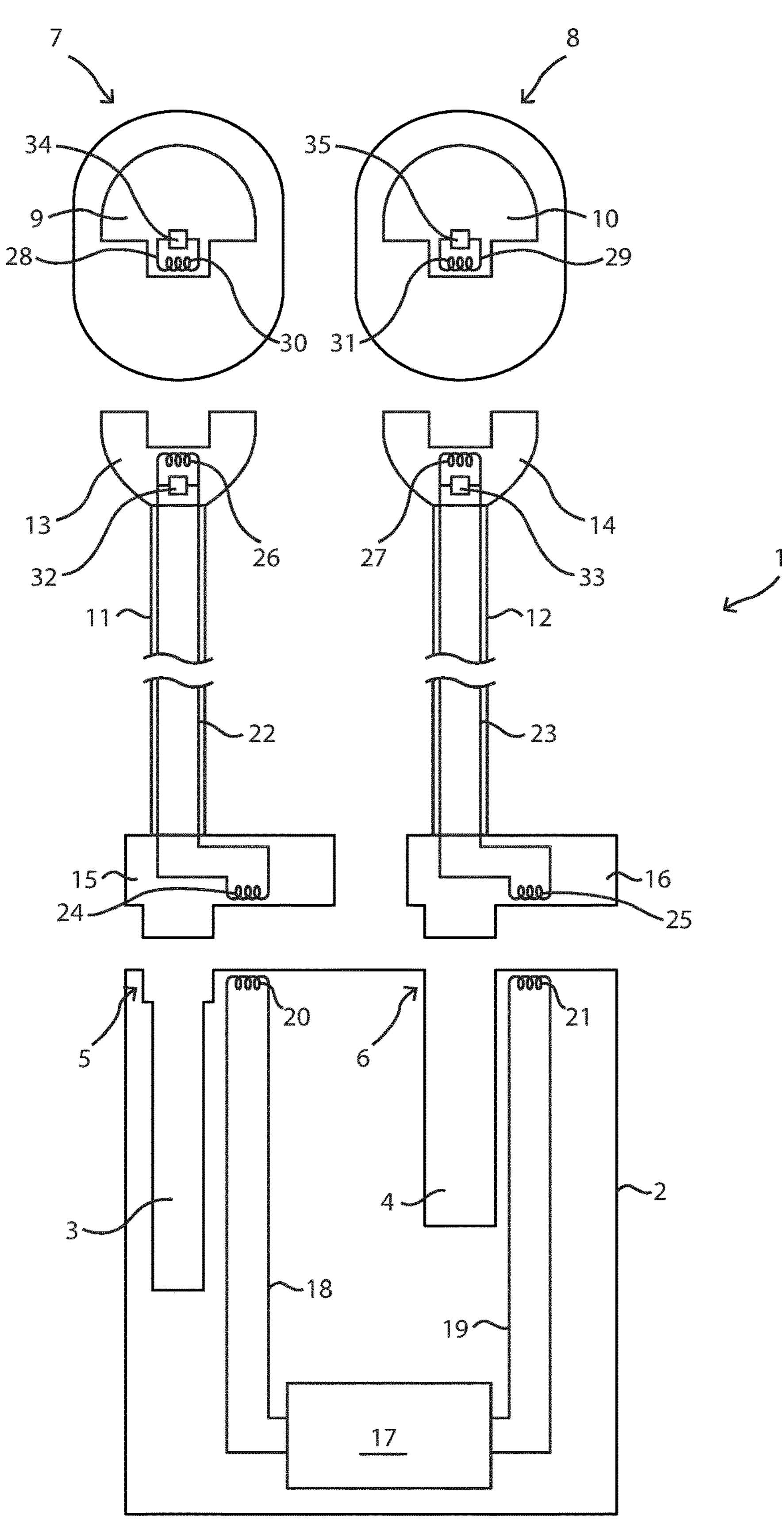

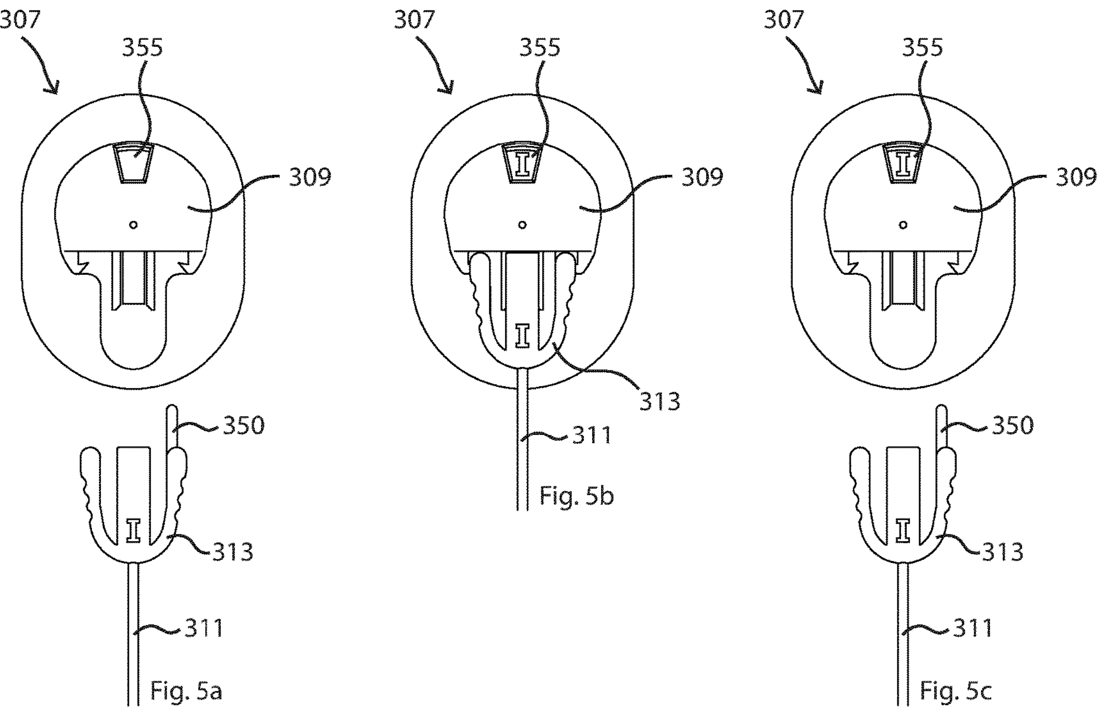
307
355
309
350
313
311
Fig. 5a
307
355
309
313
311
Fig. 5b
307
355
309
350
313
311
Fig. 5c
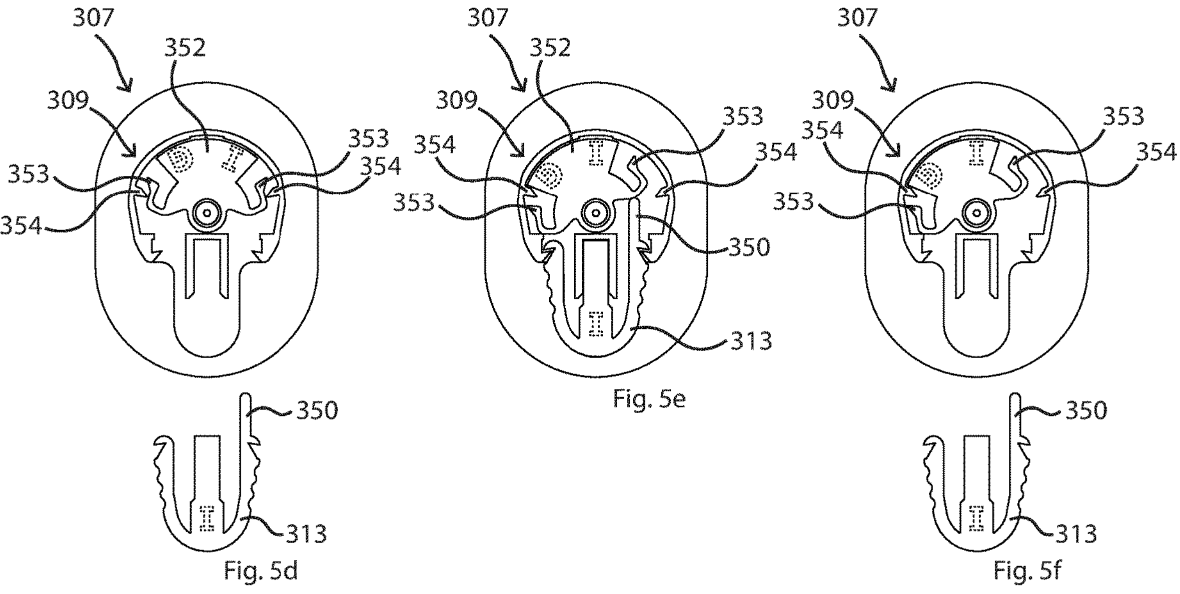
307
352
309
353
353
354
354
350
313
Fig. 5d
307
352
309
353
354
354
353
350
313
Fig. 5e
307
309
353
354
354
353
350
313
Fig. 5f

INFUSION SET, SYSTEM COMPRISING SUCH AN INFUSION SET, AND USE OF SUCH A SYSTEM

This application is a national stage filing under 35 U.S.C. 371 of pending International Application No. PCT/EP2022/059017, filed Apr. 5, 2022, which claims priority to Netherlands patent application 2027930, filed Apr. 7, 2021, the entirety of which applications are incorporated by reference herein.

The invention relates to an infusion set for a system for regulating the concentration of glucose in the blood of a person, to such a system comprising such an infusion set and to the use of such a system.

Such a system is known per se and may be used by diabetes patients for regulating the concentration of glucose in their blood. An example of such a system can be found in the international patent application WO2007/049961, but the system may be any other type of a system for regulating the concentration of glucose in the blood of a person. For example, the system may be, but not limited thereto, an artificial pancreas, a bionic pancreas, a closed loop glucose control system, a low glucose suspend system, or a hybrid closed loop control system.

An infusion set for such a system is known per se. Such an infusion set may comprise:

an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a transport element of the infusion set, and a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means.

It is noted that said infusion set comprising said infusion element and infusion means may alternatively be referred to as an injection set comprising an injection element and injection means.

Said infusion means may either be partly inserted into the body of the person, for example in particular a said cannula, catheter or needle, or may be arranged close to the body and thereby able to infuse or inject the substance into the body, for example in particular a said nozzle.

Said substance may be infused or injected into the body over a longer period of time or instantaneously.

In particular for systems supplying two different types of substances which affect the concentration of glucose in the blood of the person, such as insulin and glucagon, it is known to provide different first and second connectors for insulin and glucagon, such that it is impossible to connect a transport element for glucagon to an infusion element for insulin and vice versa. This enhances the safety of use of such a device. Such a solution is also known as mischanneling prevention. A disadvantage thereof is however that different transport elements and infusion elements have to be provided for the two different substances, which may increase the costs and/or decrease the flexibility for the user.

It is an object of this invention to at least partially overcome this disadvantage and/or to improve said known infusion set and/or system.

This object is met by an infusion set as described above that is characterized in that said infusion element is adjustable from a neutral condition to at least a first or second condition, wherein in the first or second condition the infusion element is adapted to a first or second type of transport element only.

An advantage of said infusion element being adjustable is that initially, i.e. prior to being adjusted, the infusion element is suitable for different types of transport elements, i.e. the infusion element is uniform and/or neutral. As a result thereof, only one uniform type of infusion element has to be provided, which may provide the advantage of reduced costs and/or increased flexibility. After adjusting the infusion element to either its first or second condition the infusion element is adapted to one type of transport element only, thereby providing said above described advantage of enhanced safety.

The first and second types of transport elements are different from each other, optionally after being adjusted as well, as will be described below with respect to an exemplary embodiment of the infusion set according to the invention. The first and second types of transport elements may differ from each other in any suitable way. For example, the first and second types of transport elements may each comprise a different second connector. Alternatively or additionally, the first and second types of transport elements may each comprise a different adjusting element, which adjusting element will be described in further detail below.

A system according to the invention comprising two of said infusion sets according to the invention may comprise one of said first and one of said second type of transport elements.

Adapting the infusion element to one type of transport means only may be achieved in any suitable way. For example this can by achieved by adjusting the first connector of the infusion element such that after being adjusted it can physically connect to only one type of second connector and thereby to only one type of transport element and cannot connect to another type of second connector. Alternatively or additionally this can be achieved by arranging a device of the system and/or infusion set such that it will function only, for example only supply substance, if that one type of transport element is connected to the first connector of the infusion element and not if another type of second connector is connected thereto, i.e. adapting the infusion element and thereby the device and/or infusion set to cooperate only with that type of transport element. Alternatively or additionally this can be achieved by providing an indication that the first connector of the infusion element may only be connected to that one type of transport element and not to another type of transport element, i.e. that the infusion element only matches with that one type of transport element. It is noted that these examples are not limiting and that other ways of adapting the infusion element to a certain type of transport element may be used.

"Only connect to" may include that physically the infusion element can only be connected to one of the two transport elements and not to the other transport element.

"Only cooperate with" may include that a said device of the system and/or the infusion set does only function, i.e. for example substance is supplied only, when the infusion element is connected to the correct transport element.

"Only match with" may include that an indicator is provided for indicating that the infusion element can only match with one of the two transport elements.

It is noted that any suitable part of the infusion element may be adjustable, for example the first connector thereof or any other, described or non-described part of the infusion element.

It is noted that the first and second conditions may alternatively be referred to as an insulin condition and glucagon condition, respectively.

It is noted that the infusion element may be adjusted to at least one further condition, such as for example a third and/or fourth condition. The third and/or fourth condition may for example be disconnected conditions, i.e. intermediate conditions between the neutral condition and the first or second condition, respectively, as will be described below.

It is noted that the infusion set and/or device may be arranged to not supply substance if said infusion element is in its neutral condition, or, if provided, in its third and/or fourth condition, indicating that no second connector and thereby no transport element is connected thereto.

It is noted that adjusting the infusion element may take place at any suitable moment, for example prior to, upon, or after connecting a transport element to the first connector.

It is noted that adjusting the infusion element may take place in any suitable way, for example manually and/or automatically and/or by means of an adjusting element as described below.

In an embodiment of the infusion set according to the invention at least one adjustable element is provided by means of which said infusion element is adjustable from its neutral condition to either its first or second condition.

Said adjustable element may be part of the infusion element or provided as a separate element. Such an adjustable element may be used for making the infusion element adjustable to either its first or second condition and after adjusting the adjustable element the correct transport element may be connected to the first connector or said adjustable element may be adjusted upon connecting a transport element to the first connector for the first time. If said adjustable element is provided as a separate element it may be disposable or re-usable. Such a separate adjustable element may for example be, optionally releasably, connectable to the infusion element, such that in a connected position of the adjustable element to the infusion element the infusion element can be and/or is and/or remains adjusted, and/or wherein connecting the adjustable element to the infusion element may provide the advantage of storing the adjustable element on the infusion element until a new infusion element is to be adjusted and until the adjustable element is removed and/or disconnected from the infusion element.

It is noted that throughout this text where it is indicated that the infusion element is adjusted this may also be understood as said optionally provided adjustable element being adjusted.

In another embodiment of the infusion set according to the invention at least one adjusting element is provided for adjusting the infusion element from its neutral condition to either its first or second condition.

Said adjusting element may be provided as a separate element. Such a separate adjusting element may be used for adjusting the infusion element to either its first or second condition and prior or after adjusting the infusion element the correct transport means may be connected to the first connector. Such a separate adjusting element may be disposable or re-usable. Such a separate adjusting element may for example be, optionally releasably, connectable to the infusion element for adjusting the infusion element, such that in a connected position of the adjusting element to the infusion element the infusion element is and/or remains adjusted, and/or wherein connecting the adjusting element to the infusion element may provide the advantage of storing the adjusting element on the infusion element until a new infusion element is to be adjusted and until the adjusting element is removed and/or disconnected from the infusion element.

Alternatively the adjusting element may be provided as part of the device of the system.

Alternatively said transport element, for example the second connector thereof, may comprise said adjusting element for adjusting the infusion element from its neutral condition to either its first or second condition when the second connector of the transport means is connected to the first connector.

An advantage thereof is that adjusting of the infusion element may take place simultaneously with or after connecting the second connector of the transport element to the first connector of the infusion element, such that the infusion element is adapted to that transport element of which the second connector is connected to the first connector of that infusion element.

It will be thus clear for the skilled person that "when" may be understood as "if" or "upon".

Practically the adjusting element is chosen out of at least two different adjusting elements, a first adjusting element of the two different adjusting elements being arranged for adjusting the infusion element from its neutral condition to its first condition and a second adjusting element of the two different adjusting elements being arranged for adjusting the infusion element from its neutral condition to its second condition.

In other words, a first type of adjusting element and a second type adjusting element may be provided, said two types being different from each other.

By providing said two different adjusting elements the infusion element can easily be adjusted to either its first or second condition, depending on the type of adjusting element, i.e. the first adjusting element or the second adjusting element, respectively.

Said first adjusting element may for example be provided for insulin and said second adjusting element may for example be provided for glucagon.

It is noted that for example depending on the amount and/or type of substances to be supplied by the device even further different adjusting elements may be provided.

Said at least two adjusting elements, or alternatively or additionally the at least two transport elements or second connectors thereof which may comprise these adjusting elements, may have a different appearance, such as a different shape, different colour, different text, different symbol, different feel, etc., to show to a user which adjusting element out of the at least two adjusting elements that particular adjusting element is or which adjusting element that transport element or second connector thereof comprises.

If said adjusting elements are part of the transport element or second connector thereof, a first type of transport element may be provided having said first adjusting element, and a second type of transport element may be provided having said second adjusting element.

The or each adjusting element may be embodied in any suitable way.

For example, the first adjusting element may have at least partly a different shape than the second adjusting element.

Additionally or alternatively the first adjusting element and the second adjusting element may be located at different positions and/or in different orientations on the transport elements and in particular on the second connector thereof.

As a result of the different shapes and/or different positions and/or different orientations of the first and second adjusting elements the infusion element may be adjusted to either its first or first condition.

Such embodiments may in particular be advantageous if said second connector comprises said adjusting element, such that said infusion element is adjusted upon said second connector being connected to the first connector.

It is noted that if the adjusting elements are part of a respective second connector, the second connector and/or first connector may be embodied such that the second connector can only connect to a said first connector in a specific orientation. For example, guiding means may be provided for this purpose and/or at least parts of the second connector and/or first connector may be shaped and/or sized in a specific way to achieve this effect.

In an embodiment of the infusion set according to the invention the infusion element is mechanically adjustable, for example by means of the adjustable element being moveable, wherein adjusting the infusion element comprises moving the adjustable element from a neutral position in accordance with the neutral condition to either a first or second position in accordance with the first or second condition, respectively.

An advantage of this embodiment is that the first and second positions of the adjustable element may physically limit the infusion element to be connected to one type of transport means only, because in each of the first and second position of the adjustable element only the corresponding type of second connector can connect to the first connector, which may provide a high level of safety. Practically the first connector comprises the adjustable element in this embodiment.

Moving the adjustable element to its first or second position may take place prior to connecting a transport element to the first connector or during connecting a transport element to the first connector, wherein in this last example practically the second connector of the transport element comprises said adjusting element.

This embodiment may in particular be combined with the embodiment described above in which the first adjusting element has a different shape and/or different position and/or different orientation than the second adjusting element. As a result of the shape and/or position and/or orientation of the adjusting element the adjusting element may move the adjustable element to the first or second position.

In another embodiment of the infusion set according to the invention the infusion element is electronically adjustable, for example by means of the adjustable element comprising a writable memory, wherein adjusting the infusion element comprises writing the memory with information indicative of the first or second condition, or for example by means of the adjusting element comprising a memory containing information indicative of the first or second condition such that adjusting the infusion element comprises connecting the adjusting element to the infusion element.

An advantage of this embodiment is that it may be a mechanically simple solution, wherein the mischanneling prevention is provided electronically, i.e. by using electronic components, such as for example said (writable) memory which may for example be a (writable) memory chip. Use of said electronic components may take place in such a way that the device is arranged to only function if, after being adjusted, the infusion element is connected to a correct transport element. A further advantage may be that the information written in the memory or other information that can be written in the memory may be used for other purposes, for example for determining how long a said infusion element has been in use.

In case a writable chip is provided the writable chip may be any suitable type of chip, in particular any suitable type of memory chip. For example the chip may be a write once (read many) chip, such that after the information indicative of the first or second condition is stored therein, that information cannot be rewritten. Alternatively software may be provided that may be arranged such that said information indicative of the condition cannot be rewritten. Such exemplary embodiments may in particularly be advantageous if the chip is used for only one, single-use infusion element. If said writable chip is provided as a separate element and can be reused for new infusion elements, the writable chip may be (re)written more than once, for example every time a new infusion element is installed. After writing said information indicative of the first or second condition in said memory and optionally after connecting the adjustable element comprising said memory to the infusion element it can be checked if the infusion element is connected to the correct transport element based on said information.

In case the adjusting element comprising the memory is provided the adjusting element may be a said separate element that can be, optionally releasably, connected to the infusion element for adjusting the infusion element. After connecting the memory containing said information indicative of the first or second condition to the infusion element it can be checked if the infusion element is connected to the correct transport element based on said information.

The information indicative of the first condition may for example be that the infusion element is (to be) connected to an insulin transport means and the information indicative of the second condition may be that the infusion element is (to be) connected to a glucagon transport means.

A said controller of said device may communicate via wires or wirelessly with the memory or chip for reading said information therefrom and optionally writing said memory or chip.

For example, communication with the memory or chip may take place via electronical or electrical circuits. In such an embodiment preferably each of the controller, the transport element, and the infusion element may comprise at least one electrical or electronical circuit or part thereof, wherein communication between the circuits for example takes place via electromagnetic coils or other suitable communication and/or transfer means or wherein said parts form a completed circuit after connecting the transport element to the device and to the infusion element. The electromagnetic coils may be arranged such that after connecting, in particularly after correctly connecting, the transport element to the device and the infusion element, the electromagnetic coils of each pair at each connection are in a position in which information can be exchanged there between, and may in particular be arranged close to each other and/or extend parallel and/or aligned with respect to each other.

In such an embodiment the circuit (part) of the transport element may comprise conductive wires that extend along the transport means between the two outer ends and/or connectors of the transport element for providing communication between the device and the second connector and/or the infusion element, wherein the wires may for example be incorporated into the material of the transport means or may be arranged at the inner or outer side of the transport means, in such a way that these are insulated from the substance.

Alternatively or additionally, communication between the device and the memory or chip may take place wirelessly, i.e. not via any and in this case not provided wires of the transport element, for example using transmitters, RFID, or other suitable means.

If communication takes place via the transport element, writing the chip by the controller may take place based on information to which port of the device a said transport means is connected, because each port is located near and/or allocated to a respective receiving space that is able to (correctly) accommodate only one type of reservoir containing either insulin or glucagon, such that the port is allocated to insulin or glucagon only. It is therefore possible to write said chip with information indicative of the first or second condition, i.e. insulin or glucagon, based on information of the port. It is noted that a further definition and/or description of said ports is given below. Alternatively the transport means may also comprise a memory chip, for convenience further referred to as the second memory or chip, which second memory or chip comprises information on the type of transport element, i.e. insulin or glucagon, wherein the information that is written in the writable chip is based on information of the second memory or chip.

It is noted that said receiving spaces being able to (correctly) accommodate one type of reservoir only may be achieved in any desired way. For example this may be achieved by providing two receiving spaces that have a different shape and/or size with respect to each other, such that each said receiving space is arranged for receiving one type of reservoir only, for example only a glucagon reservoir or insulin reservoir. This way it may be prevented that the reservoirs are accommodated in the wrong receiving space. Alternatively the receiving spaces may be similar in shape and/or size, but a detection system may be provided for detecting if the correct reservoir is accommodated in the correct receiving space. Alternatively it may be prevented in any other suitable way that the reservoirs are accommodated in the wrong receiving space.

If communication takes place wirelessly, i.e. not via the transport element, for example using transmitters, RFID, or other suitable means, writing the writable chip may take place based on information of a said second memory or chip of the transport element, similar as described above.

After storing the information in the writable memory or chip or after connecting the memory or chip to the infusion element the device may be arranged to only function if it reads the same information, i.e. indicative of the same first or second condition, in combination with the same transport element or a transport element of the same type, i.e. suitable for either insulin or glucagon. Checking whether the infusion element is connected to the same (type of) transport element may be determined based on information to which port of the device the transport element is connected or via the information of the second memory or chip of the transport element, similar as explained above with respect to writing the writable chip.

Said device and in particular the controller thereof may comprise a memory for storing the information of the (writable) memory or chip and/or second memory or chip. The memory of the device may be reset when replacing the infusion element and/or transport element for a new infusion element and/or transport element.

The (writable) memory or chip and/or second memory or chip may be passive and for example powered by the device. Alternatively, said chip and/or second chip may be part of a circuit comprising a power source, such as a battery.

It is noted that a or each glucose sensor element of the device may comprise a transmitter for transmitting glucose information to the device. Such a glucose sensor element may be combined with the infusion element as one sensor and infusion element and communication between the sensor and infusion element and the device and/or transport means may then take place via the transmitter of the sensor and infusion element. Alternatively the infusion element may be located near said glucose sensor, such that the transmitter may wirelessly communicate with both the infusion element and in particular the chip thereof and the device, for example via RFID.

It is noted if a said second memory or chip is provided the memory or chip of the infusion element may alternatively be referred to as the first memory or chip, in order to avoid confusion between the two memories or chips.

As will be clear from the above embodiments, the neutral, first, second, and optionally other conditions of the first connector can be any suitable conditions. For example the conditions can be said different positions of the adjustable element or said different information as stored in the memory.

Additionally or alternatively at least the first and second conditions are or comprise different indicators for indicating the first or second condition, respectively, of the infusion element.

The indicator may be any suitable indicator, such as for example a visual and/or tactile indicator. As an particular example, different colours or symbols may be used for indicating the different conditions, which colours or symbols preferably match with the colour or symbol of the second connector and/or transport element comprising that second connector. Alternatively or additionally the name of the substance may be indicated.

It is noted that if only said visual indicator is provided it is possible to use said device with a wrong combination of infusion element and transport means. The level of safety is thus less than in other described embodiments. However, this level of safety may be sufficient.

Practically, said infusion element may be embodied such that it cannot be adjusted from its first or second condition back to its neutral condition, at least not without performing a specific action, such as for example resetting said adjustable element, for example by resetting or overwriting a said memory.

An advantage thereof is that after adjusting the infusion element that infusion element cannot be adjusted back into its condition of being suitable for different types of transport elements, but remains adapted to that type of transport element only.

Said infusion element can in such an embodiment be seen as a uniform and/or neutral one-way adjustable infusion element.

In an electronical embodiment this may for example be achieved by providing a write once read many chip and/or by providing software that prevents overwriting said information. In a mechanical embodiment this may for example be achieved by providing a locking mechanism that locks the infusion element in its adjusted condition, i.e. in the first or second condition, or at least prevents that the infusion element returns to the neutral condition. Such a locking mechanism may for example comprise at least one locking protrusion and/or at least one finger. Such a locking protrusion and/or finger may be embodied such that the finger may be moved beyond the locking protrusion when moved in one direction, but cannot be moved beyond the locking protrusion when moved in an opposite position and is therefore locked by said locking protrusion. Such at least one finger may be part of the adjustable element and the locking protrusion may be part of a non-moveable part of the infusion element.

It is noted that if a said adjustable element is provided as a separate element, said adjustable element may optionally be adjusted back into its neutral condition, such that said adjustable element may be re-usable for a new infusion element.

It is noted that if said infusion element is adjustable to at least one further condition, the infusion element may optionally remain adjustable between either the first or second condition and said at least one further condition. For example, said at least one further condition may be a condition in which the infusion element is not connected to a said second connector at that time, such that upon disconnecting the second connector from the first connector the infusion element is adjusted from the first or second condition to this further condition, and upon reconnecting the same or a replacement transport element with a second connector of the same type the infusion element may be adjusted back to its previous first or second condition.

It is further noted that the infusion element may be embodied such that it cannot be adjusted from its first or second condition to the other of the first and second condition, at least not without performing a specific action such as resetting or overwriting a said memory.

In yet another embodiment of the infusion set according to the invention, the inlet end of the transport element is connectable to a port of said device, and wherein each transport element is adapted to only one port out of two ports of said device.

An advantage of this embodiment is that as a result of the transport means being adapted to only one port of the pump, said transport means can only transport one type of substance. This further enhances the safety of the device.

It is noted that this embodiment of the infusion set is in particular suitable for a device accommodating two different reservoirs, for example one reservoir containing insulin and the other reservoir containing glucagon.

Said transport element being adapted to one port only may for example be achieved by a transport element that can only connect to and/or cooperate with and/or match with one of the two ports.

"Only connect to" may include that physically the inlet end of the transport element can only be connected to one of the two ports and not to the other port.

"Only cooperate with" may include that the device and/or infusion set does only function, i.e. for example substance is supplied only, when the transport element is connected to the correct port.

"Only match with" may include that an indicator is provided for indicating that the transport element can only match with one of the two ports.

In addition or alternatively to these three examples any other suitable way of adapting the transport element to only one port out of two ports of said pump may be provided.

In this embodiment the first and second port of the device may only accommodate the first and second reservoir respectively, and not the other reservoir. This may for example be achieved by said device having two different receiving spaces, each for receiving and accommodating a said reservoir, wherein each said a receiving space may have a certain shape and/or size for (suitably) receiving and accommodating only one type of reservoir. In accordance with this example, the first and second reservoirs may for example have a certain (different) shape and/or (different) size.

In the above embodiment the transport element may be a pre-set transport element that is adapted to one port only, or a transport element that is adjustable and after being adjusted is adapted to one port only.

In other words, in an embodiment of the of the infusion set according to the invention said transport element may be adjustable from a neutral condition to a first or second condition, wherein in the first or second condition the transport element is adapted to a first or second port, respectively.

Advantages of this embodiment may be similar to the advantages described with respect to the adjustable infusion element, i.e. said transport element may be neutral prior to being adjusted.

Adjusting the transport element may take place in any suitable way, for example in a similar manner as described above with respect to the infusion element.

Optionally said transport element may comprise a second adjustable element that is part thereof or can for example be connected thereto that is adjustable from said neutral condition to said first or second condition.

Said second adjustable element may be embodied in any suitable way, for example in a similar manner as described above with respect to the adjustable element of the infusion element.

As will be clear for the skilled person, "second" is used here to differentiate from the adjustable element of the infusion element, which may also be referred to as the first adjustable element.

Practically each said transport element may comprise a third connector that is arranged at the inlet end of the transport means by means of which the transport element can be connected to a said port.

Practically it may be the third connector that may be adjustable from said neutral condition to said first or second condition. Adjusting the third connector may take place in any suitable way, for example in a similar manner as described above with respect to the infusion element.

Practically the device may be arranged such that it can adjust each of said transport element, for example by means of a said controller of the device. Additionally or alternatively said device, for example the ports thereof, may comprise a second adjusting element for adjusting the transport element from its neutral condition to either its first or second condition when said transport element is connected thereto.

Said second adjusting element may be embodied in any suitable way, for example in a similar manner as described above with respect to the adjusting element of the transport means.

As will be clear for the skilled person, "second" is used here to differentiate from the adjusting element described above, which may also be referred to as the first adjusting element.

In a preferred embodiment said transport element is able to adjust said infusion element after being adjusted itself.

For example if the adjustment of the transport element and infusion element takes place electronically, this may be achieved by providing a writable chip as the second chip of the transport element or by providing a pre-written chip as a separate element that can be connected to the transport element. The controller may write the writable chip with information on the type of transport element, i.e. insulin or glucagon, or the chip may be pre-written with such information, wherein the information written in the (first) writable chip of the infusion element is then based on information of the second writable chip.

In a mechanical embodiment it can be foreseen that after or upon mechanically adjusting the transport element, in particular the third connector thereof, the adjusting element of the second connector of the transport element is adjusted such that it is able to adjust the infusion element to either its first or second condition. In order to achieve this a mechanical linkage may be provided between the third and second connector of the transport element and in particular between the second adjustable element of the third connector and the adjusting element of the second connector.

In an embodiment of the infusion set according to the invention the infusion element is adjustable between its first or second condition and a third condition in which the first connector is not connected to a second connector or, optionally, to a wrong second connector.

Such an embodiment may provide at least one of the following advantages. The device and/or infusion set may be arranged to only function, for example only supply substance, if the infusion element is in its first or second condition and not if the infusion element is in its third condition. It may be indicated to a user of the device that the infusion element is in its third condition, such that the user may see that a (correct) second connector needs to be connected to the first connector.

The third condition may for example be detected electronically or mechanically.

Alternatively or additionally an indicator may be provided indicating that the first connector is in its third condition.

This may for example be achieved by a moveable adjustable element which connects to an indicator and which can move into a third position when the second connector is disconnected from the first connector, thereby also adjusting the indicator to show this third condition.

The above described embodiments may relate to a first invention of this application.

A second invention of this application relates to an infusion set for a device for regulating the concentration of glucose in the blood of a person, said infusion set comprising:

- an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a transport element of the infusion set, and
- a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means,
- wherein said infusion element is adjustable between a non-connected condition when the second connector is not connected to the first connector and a connected condition when the second connector is connected to the first connector.

Such an embodiment may provide at least one of the following advantages. The device and/or infusion set may be arranged to only function, for example only supply substance, if the infusion element is in its connected condition and not in its non-connected condition. Alternatively or additionally it may be indicated to a user of the device that the infusion element is in its non-connected condition, such that the user may see that a second connector needs to be connected to the first connector.

The non-connected condition may correspond to the third condition and the connected condition may correspond to the first or second condition of the first invention of this application.

Said infusion set according to this second invention may comprise any one or more features of the infusion set according to the first invention as described above or according to any of the devices described below, alone or in any combination. The advantages described above and/or below apply to this second invention respectively.

A third invention of this application relates to an infusion set for a device for regulating the concentration of glucose in the blood of a person, said infusion set comprising:

- an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a transport element of the infusion set, and
- a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means,
- wherein said transport element is adjustable from a neutral condition to a first or second condition, wherein in the first or second condition the transport element is adapted to a first or second port, respectively.

Said infusion set according to this third invention may comprise any one or more features of the infusion set according to the first invention and/or the second invention as described above or according to any of the devices described below, alone or in any combination. The advantages described above apply to this third invention respectively.

As described above, the invention also relates to a system for regulating the concentration of glucose in the blood of a person, said system comprising:

- two infusion sets according to the invention as described in any one or more of the embodiments described above and/or having any one or more of the above described features and/or according to the second invention and/or according to the third invention;
- a device for selectively supplying at least two substances contained in respective reservoirs, said device comprising:

at least two receiving spaces for accommodating a respective reservoir, at least two ports for connecting to a respective transport element, and a controller for controlling said device such that a certain amount of a said substance is supplied and thereby infused into the body of the person, wherein the inlet end of each of the transport elements is connectable to a said port of said device.

The advantages of the infusion set according to the first invention and/or the second invention and/or the third invention as described above apply to the system according to the invention as well.

Each said port may for example be defined by any suitable interface and/or connector for providing a connection between the device and the inlet end of the transport element, and in particular between the device and a said third connector of the transport element. Said ports may be arranged in the vicinity of a respective receiving space, for example near a receiving end of a respective receiving space, such that when the inlet end or third connector is connected to a respective port a medium through flow connection between the reservoir contained in the receiving space and the transport element is established.

The substance may be a substance which affects the concentration of glucose in the blood of the person. For example a such substance may be insulin and/or glucagon.

The amount of substance to be supplied may be a calculated amount or a set amount as inputted by a user of the device.

The controller may be any suitable controller, such as a (micro) processor.

In an embodiment of the system according to the invention the controller may be arranged to control the device such that substance is only supplied if the infusion element is connected to a correct transport element.

In an embodiment of the system according to the invention the controller may be arranged for reading and optionally writing the memory or chip and/or second memory or chip as described above.

In an embodiment of the system according to the invention said device and in particular the controller thereof may comprise a memory for storing information, for example of the (writable) memory or chip and/or second (writable) memory or chip. The memory of the device may optionally be reset and/or overwritten when replacing the infusion element and/or transport element for a new infusion element and/or transport element.

The device may be arranged to only function if it reads the same information, i.e. indicative of the same first or second condition, in combination with the same transport element or a transport element of the same type, i.e. suitable for either insulin or glucagon, as described above.

Optionally said device may comprise a power supply for powering said device and/or any one or more of the above described chips.

The system may further comprise at least one glucose sensor element comprising a glucose sensor.

A or each glucose sensor element of the system may comprise a transmitter for transmitting glucose information to the device. Such a glucose sensor element may be combined with the infusion element as one sensor and infusion element and communication between the sensor and infusion element and the device and/or transport element may then take place via the transmitter of the sensor and infusion element, as described above. Alternatively the infusion element may be located near said glucose sensor, such that the transmitter may wirelessly communicate with both the infusion element and in particular the memory thereof and the device, for example via RFID.

Said system, and in particular the device or infusion sets thereof, may comprise any one or more features as described above with respect to the infusion set of the first, second or third invention, alone or in any suitable combination.

In an embodiment of the system according to the invention the infusion sets provided are infusion sets according to at least claim 12, wherein the device is arranged for adjusting the transport element to its first or second condition.

Advantages of this embodiment may be similar to the advantages described with respect to the adjustable infusion element, i.e. said transport element may be neutral prior to being adjusted.

Adjusting the transport element may take place in any suitable way, for example in a similar manner as described above with respect to the infusion element.

Optionally said transport element may comprise a second adjustable element that is part thereof or can for example be connected thereto that is adjustable from said neutral condition to said first or second condition.

Said second adjustable element may be embodied in any suitable way, for example in a similar manner as described above with respect to the adjustable element of the infusion element.

Practically each said transport element may comprise a third connector arranged at the inlet end of the transport means by means of which the transport means can be connected to a said port.

Practically it may the third connector that may be adjustable from said neutral condition to said first or second condition. Adjusting the third connector may take place in any suitable way, for example in a similar manner as described above with respect to the infusion element.

Practically the device may be arranged such that it can adjust each of said transport elements, for example by means of a controller of the device. Additionally or alternatively said device, for example the ports thereof, may comprise a second adjusting element for adjusting the transport element or adjustable element therefrom from its neutral condition to either its first or second condition when said transport element is connected thereto.

Said second adjusting element may be embodied in any suitable way, for example in a similar manner as described above with respect to the adjusting element of the transport element.

In an embodiment of the system according to the invention the infusion sets provided are infusion sets according to at least claims 4 and 12, and wherein upon adjusting the transport element to its first or second condition the adjusting element of the transport element is able to adjust the infusion element from its neutral condition to either its first or second condition and/or the infusion element is adjusted from its neutral condition to either its first or second condition.

For example if the adjustment of the transport element and infusion element takes place electronically, this may be achieved by providing a writable memory or chip as the second memory or chip of the transport element or by providing a pre-written memory or chip as a separate element that can be, optionally releasably, connected to the transport element. The controller may write the writable second memory or chip with information on the type of transport means, i.e. insulin or glucagon, or said second memory or chip may be pre-written with said information, wherein the information written in the (first) writable memory or chip of the infusion element is then based on information of the second memory or chip.

In a mechanical embodiment it can be foreseen that upon or after mechanically adjusting the transport element, in particular the third connector thereof, the adjusting element of the second connector of the transport means is adjusted such that it is able to adjust the infusion element to either its first or second condition and/or said infusion element is adjusted to either its first or second condition. In order to achieve this a mechanical linkage may be provided between the third connector of the transport means and the second connector of the transport element and/or the infusion element and in particular between the second adjustable element of the third connector and the adjusting element of the second connector and/or the infusion element. Such a mechanical linkage may for example be provided via the transport means and/or by temporarily connecting or bringing the second connector to or in contact with the third connector.

Adjusting the adjusting element of the second connector may for example comprise moving the adjusting element to a first or second position, in which first or second position the adjusting element is able to adjust the adjustable element to its first or second condition, respectively.

A fourth invention of this application relates to a system for regulating the concentration of glucose in the blood of a person, said system comprising:

two infusion sets, each infusion set comprising:
- an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a transport element of the infusion set, and
- a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means, a device for selectively supplying at least two substances contained in respective reservoirs, said device comprising:
- at least two receiving spaces for accommodating a respective reservoir,
- at least two ports for connecting to a respective transport element, and
- a controller for controlling said device such that a certain amount of a said substance is supplied and thereby infused into the body of the person, wherein the inlet end of each of the transport element is connectable to a said port of said device, and wherein each said transport means element from a neutral condition to a first or second condition, and wherein the device is arranged for adjusting the transport elements to the first or second condition.

Advantages of such a system are described above.

Practically the device may be arranged such that it can adjust each of said transport elements, for example by means of a controller of the device. Additionally or alternatively said device, for example the ports thereof, may comprise a second adjusting element for adjusting the transport elements from its neutral condition to either its first or second condition when said transport element is connected thereto.

Said second adjusting element may be embodied in any suitable way, for example in a similar manner as described above with respect to the adjusting element of the transport means.

Said system according to the fourth invention may comprise any one or more of the features as described above with respect to any of the described infusion sets and/or systems, alone or in any suitable combination.

The invention also relates to the use of a system according to any one or more of the embodiments described above and/or having any one or more of the above described features, comprising the steps, to be performed in any suitable order, of:

a) providing a system according to any one or more of the embodiments described above and/or having any one or more of the above described features;
b) connecting the inlet end of the first transport element to the first port of said device and the inlet end of the second transport element to the second port of said device;
c) adjusting the first infusion element from a neutral condition to the first condition and the second infusion element from a neutral condition to the second condition;
d) connecting the second connector of the first transport element to the first connector of the first infusion element and the second connector of the second transport element to the first connector of the second infusion element.

The steps may be performed in any suitable order. Practically step a) is performed prior to steps b), c) and d). Step b) is preferably performed prior to step c) and/or d), but alternatively step c) and/or d) may be performed prior to step b).

In an embodiment of the use of the device step c) is performed by performing step d). This may in particular be the case when the second connector comprises said adjusting element as described above.

Steps b) and/or c) and/or d) may comprise two sub-steps. For example, step b1) may comprise the step of connecting the inlet end of the first transport element to the first port of said device and step b2) may comprise the step of connecting the inlet end of the second transport element to the second port of said device. For example, step c1) may comprise the step of adjusting the first infusion element from a neutral condition to the first condition and step c) may comprise the step of adjusting the second infusion element from a neutral condition to the second condition. For example, step d1) may comprise the step of connecting the second connector of the first transport element to the first connector of the first infusion element and step d2) may comprise the step of connecting the second connector of the second transport element to the first connector of the second infusion element. In such an embodiment steps b1), c1) and d1) may be performed as one sequence and steps b2), c2) and d2) may be performed as a second sequence, i.e. the steps are performed per substance, but any other suitable sequence is possible.

Use of the system according to the invention may comprise any further step relating to any of the above described embodiments of the infusion set and/or system according to the invention, which steps will be apparent for the skilled person.

For example, said use may comprise a further step of adjusting the transport element from its neutral condition to its first or second condition. This step may be performed prior to or simultaneous with step b).

Figure 1B:
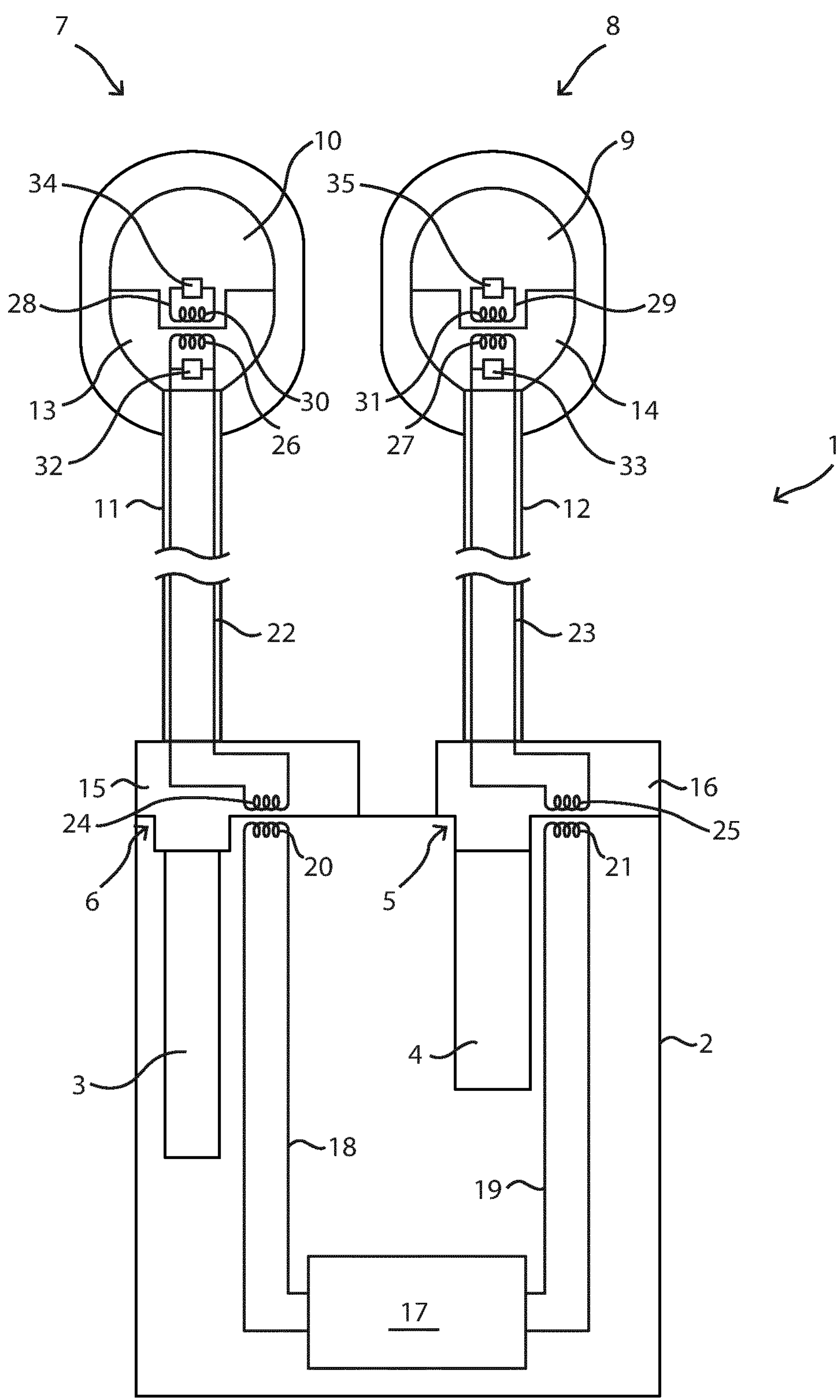
Figure 2A:
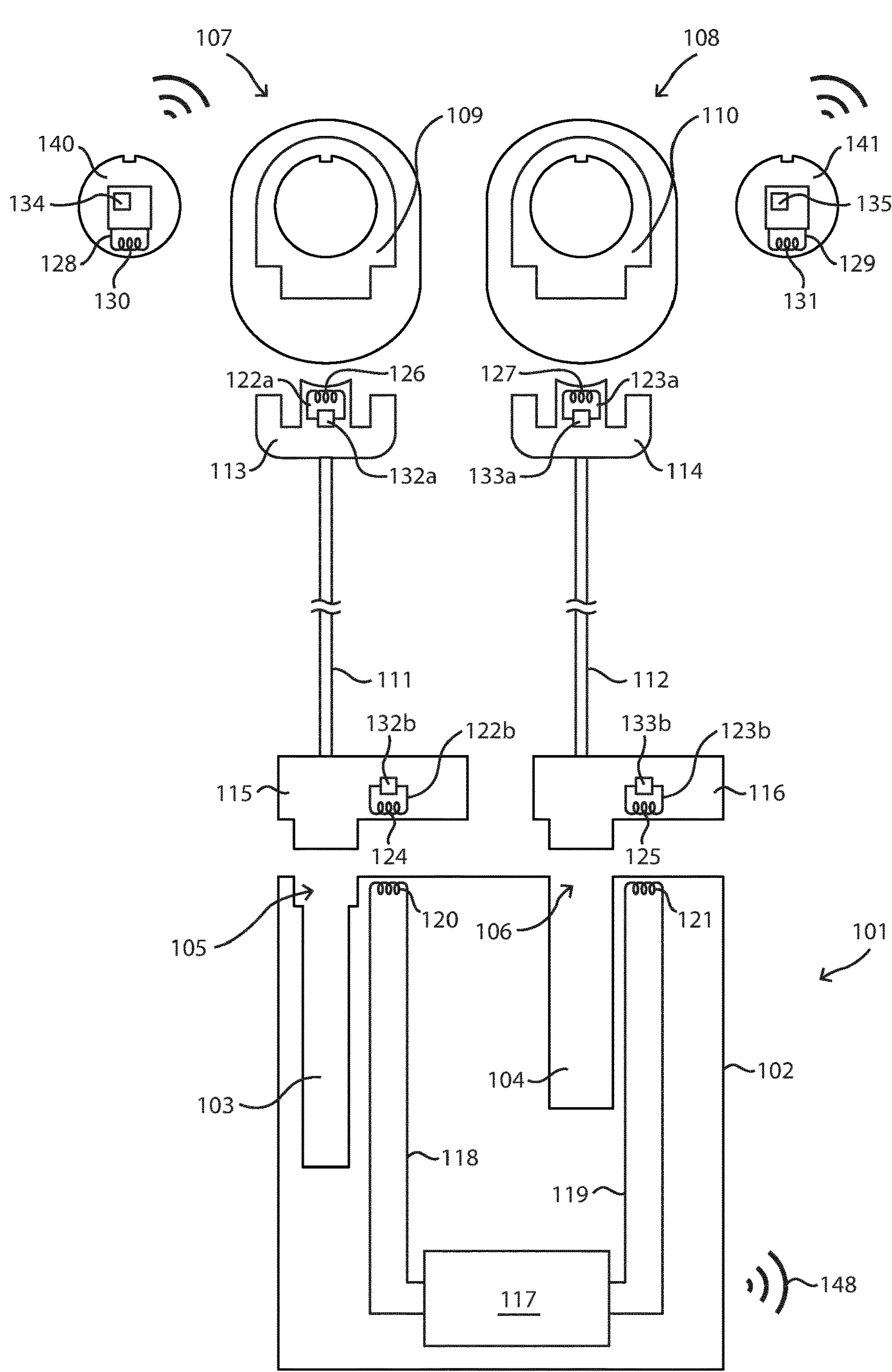
Figure 2B:
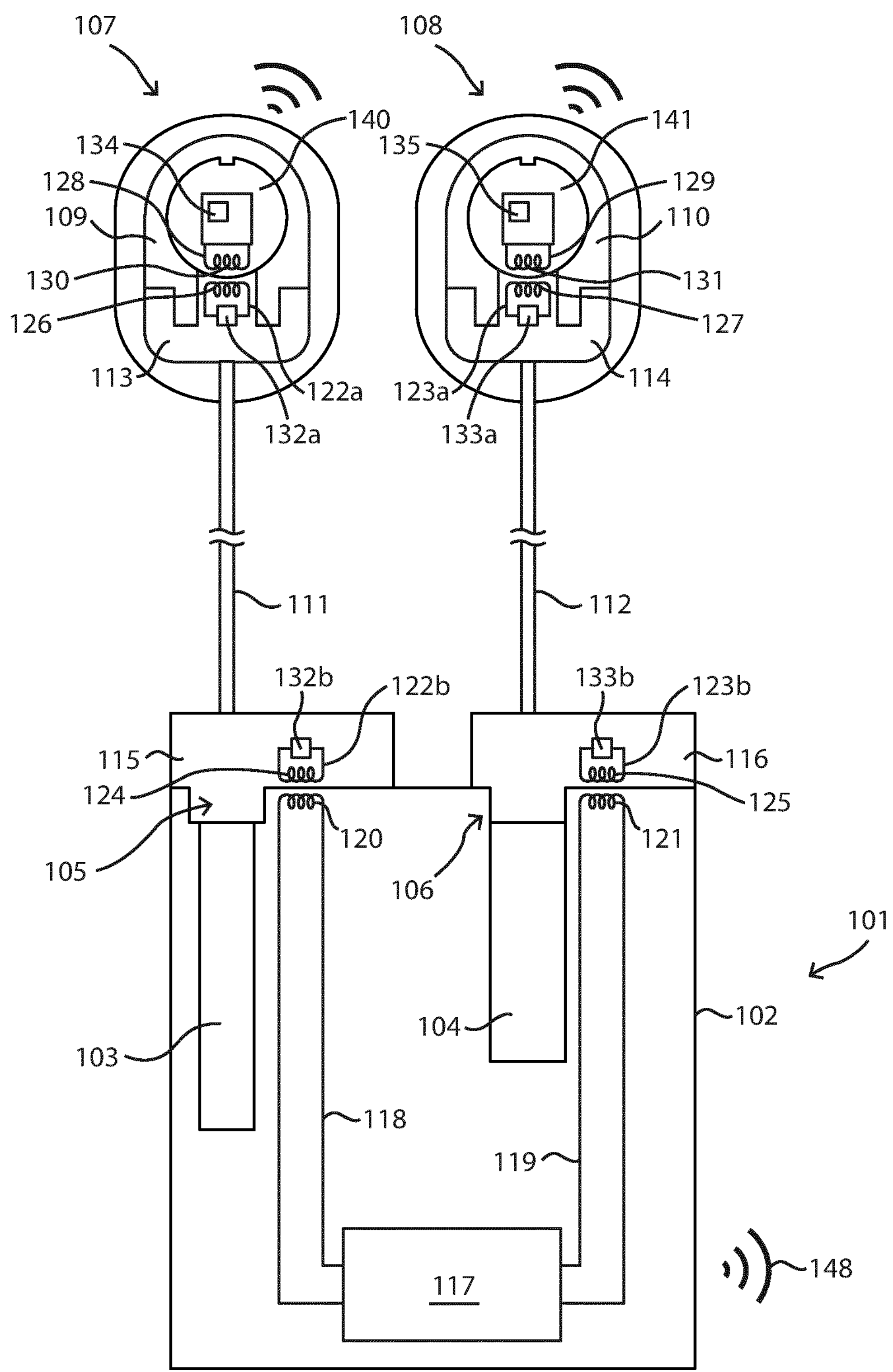
Figure 3B:
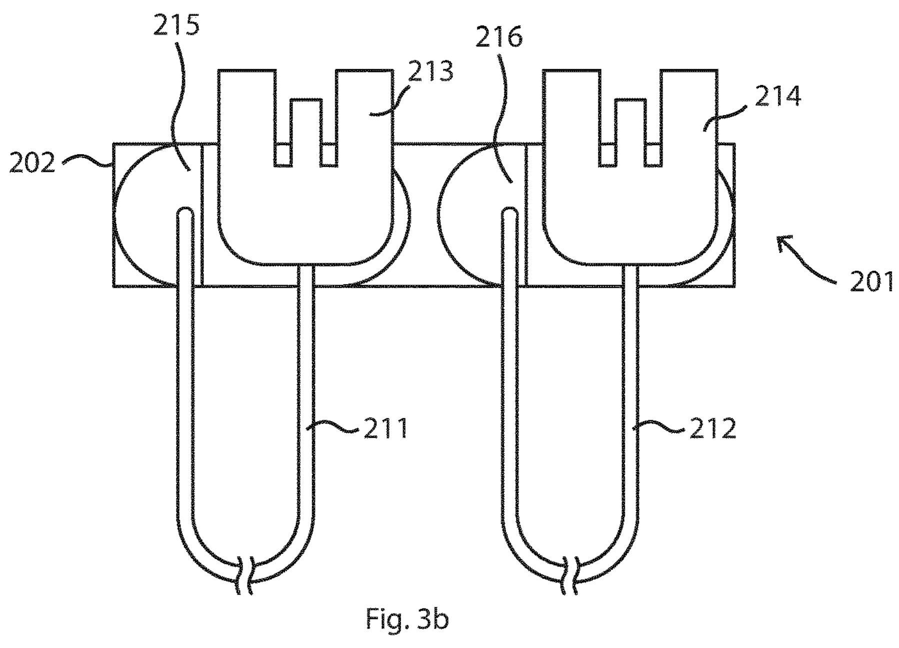
Figure 3A:
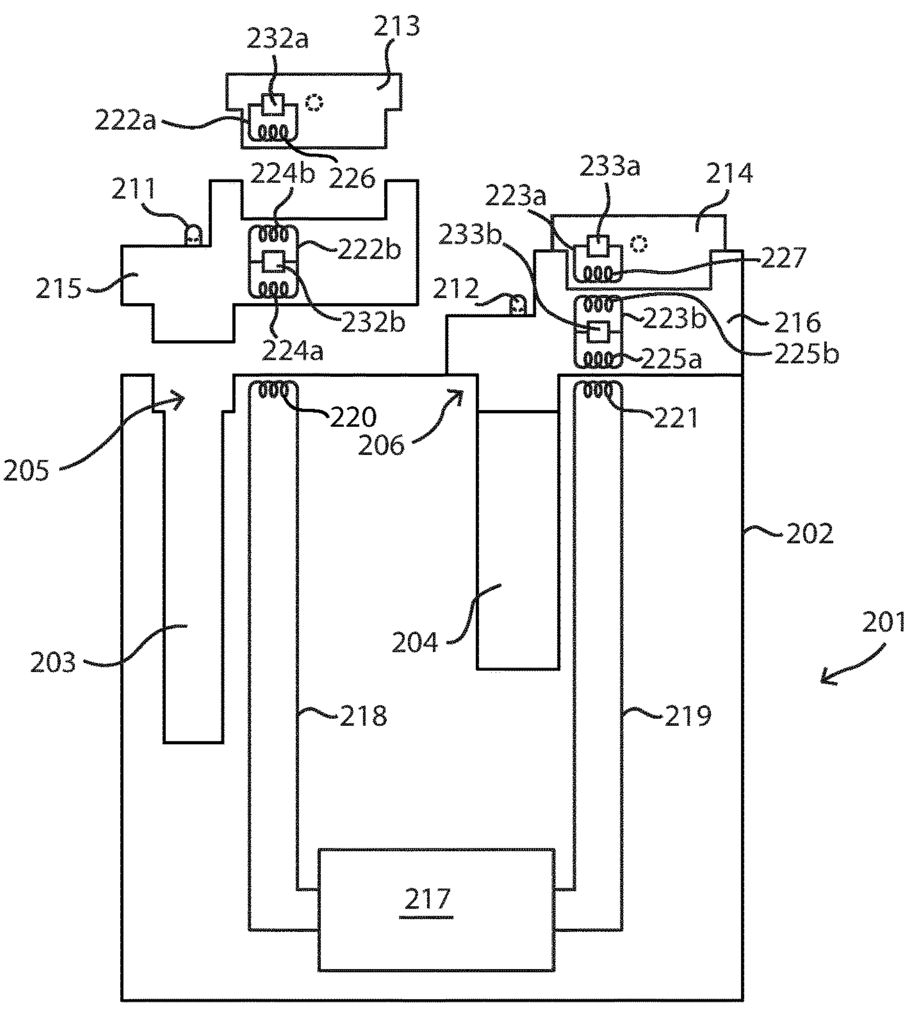
Figure 4A:
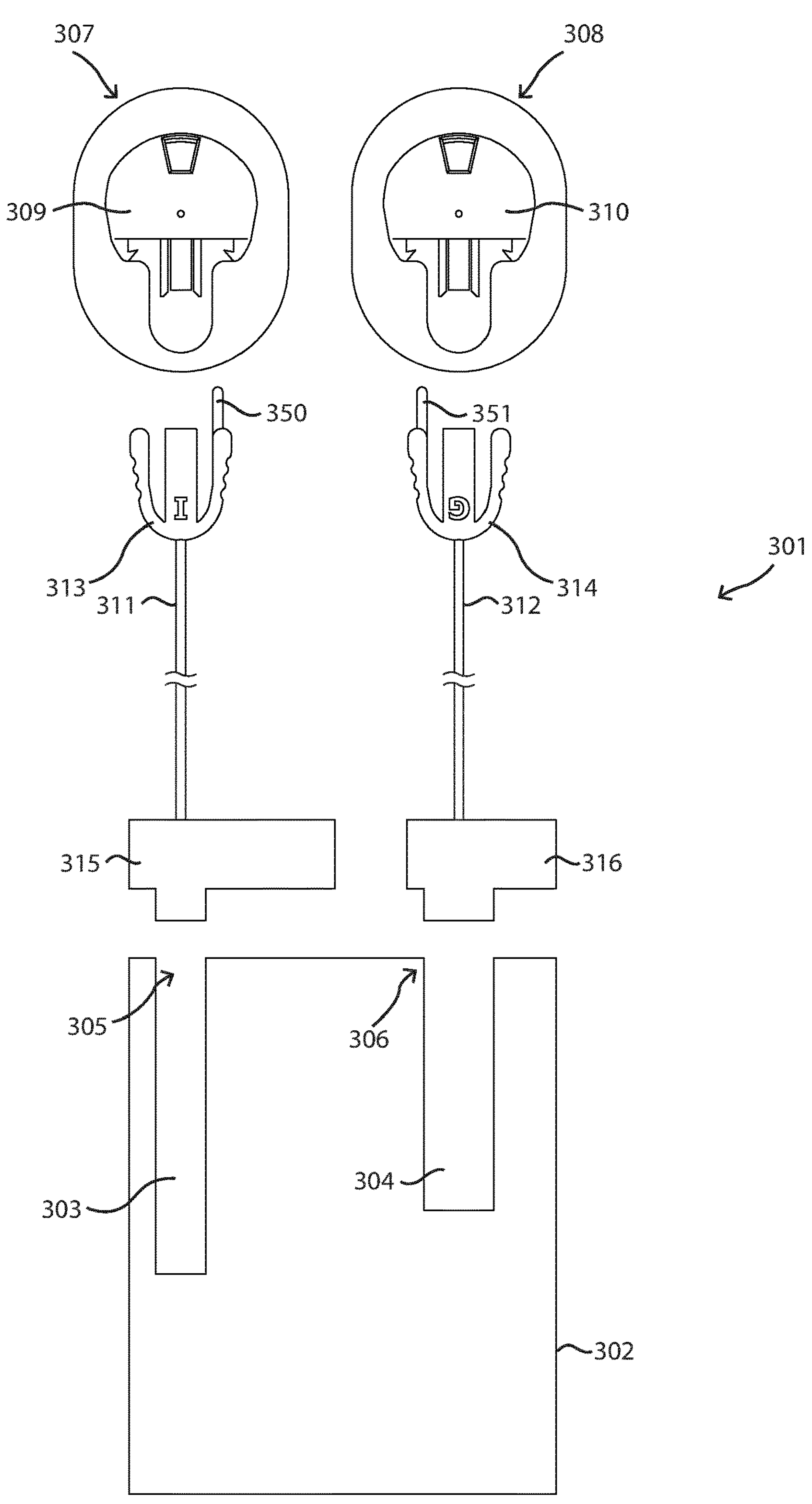
Figure 4B:
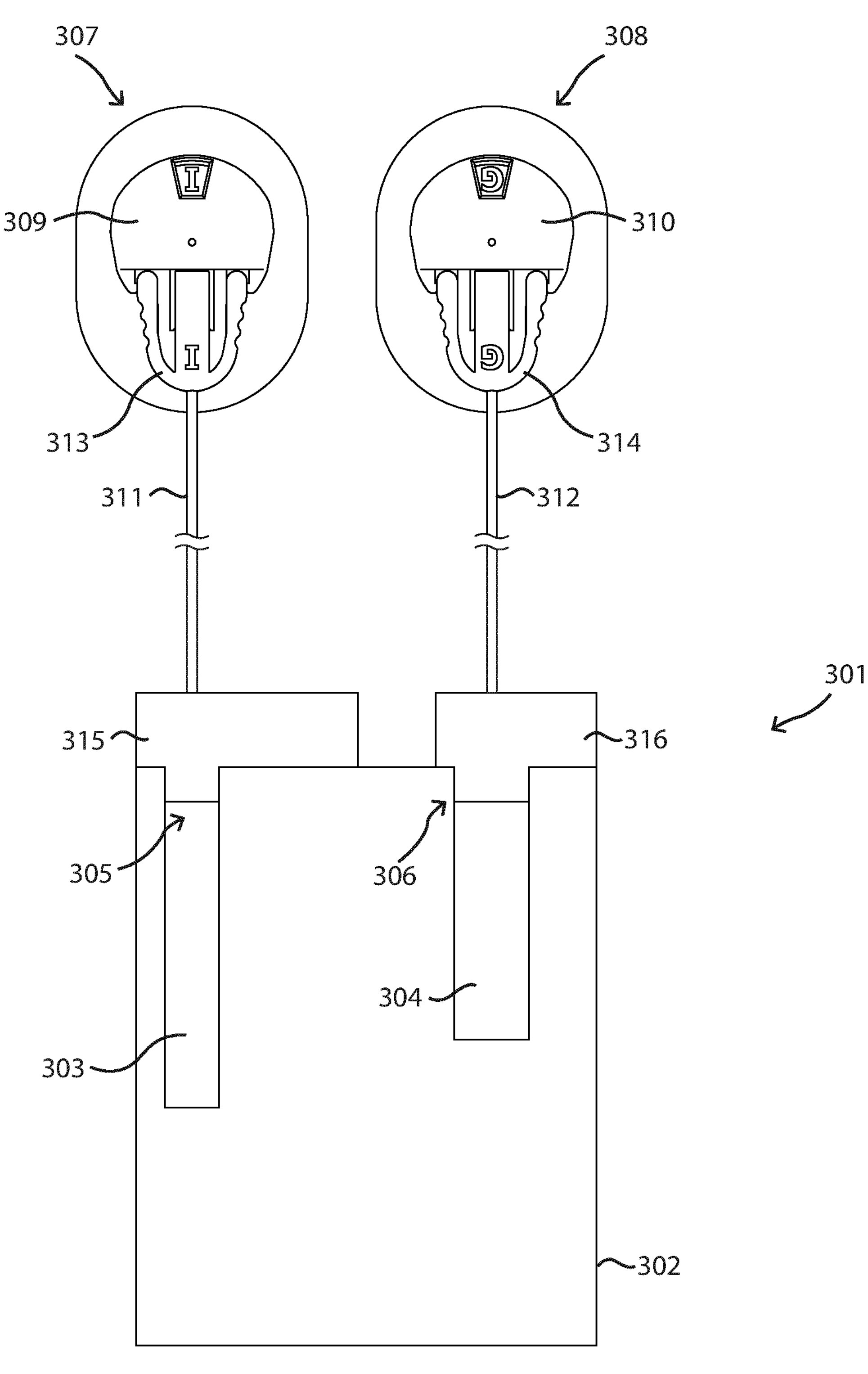
Figures 6A, 6B:
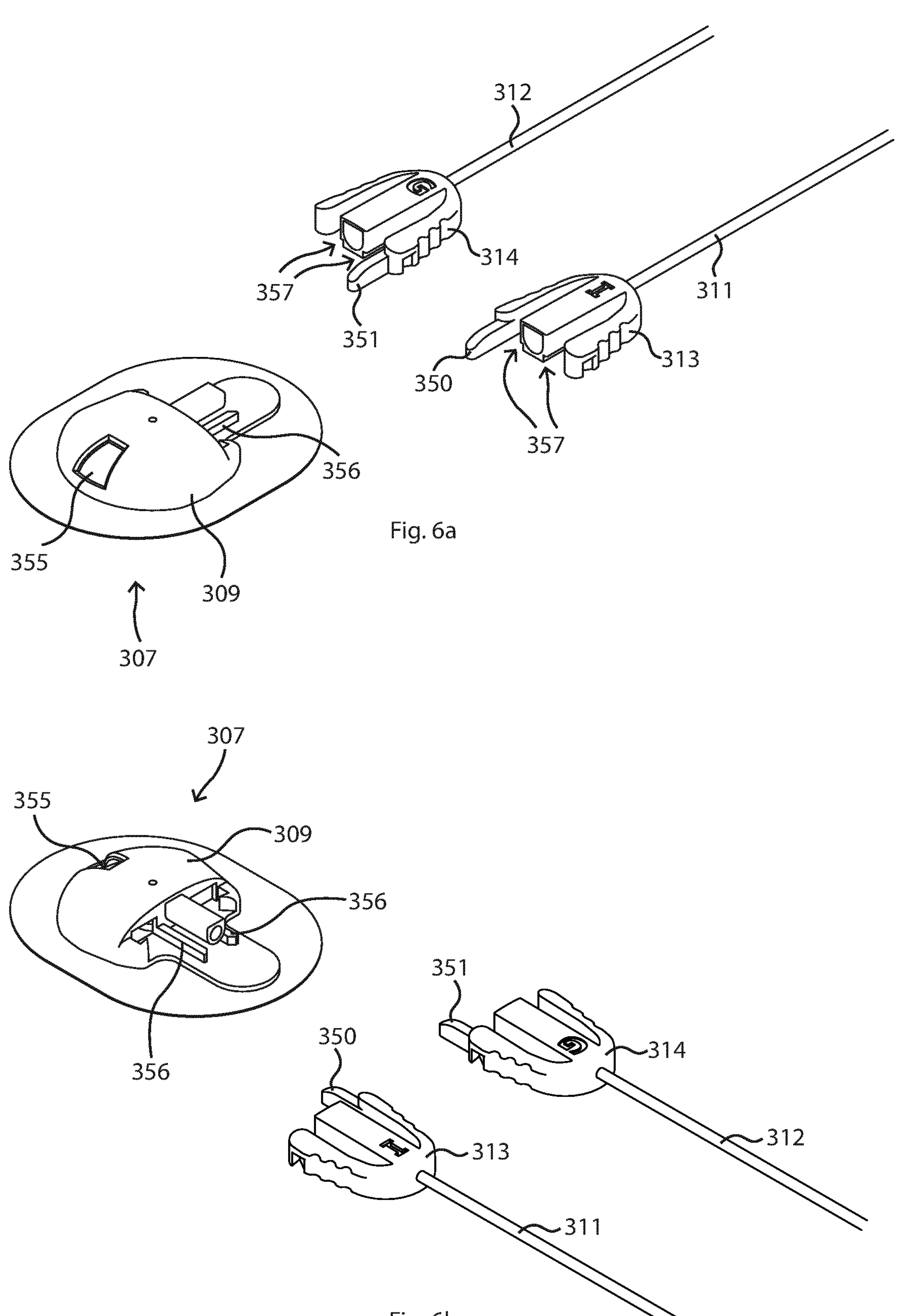
Figure 7A:
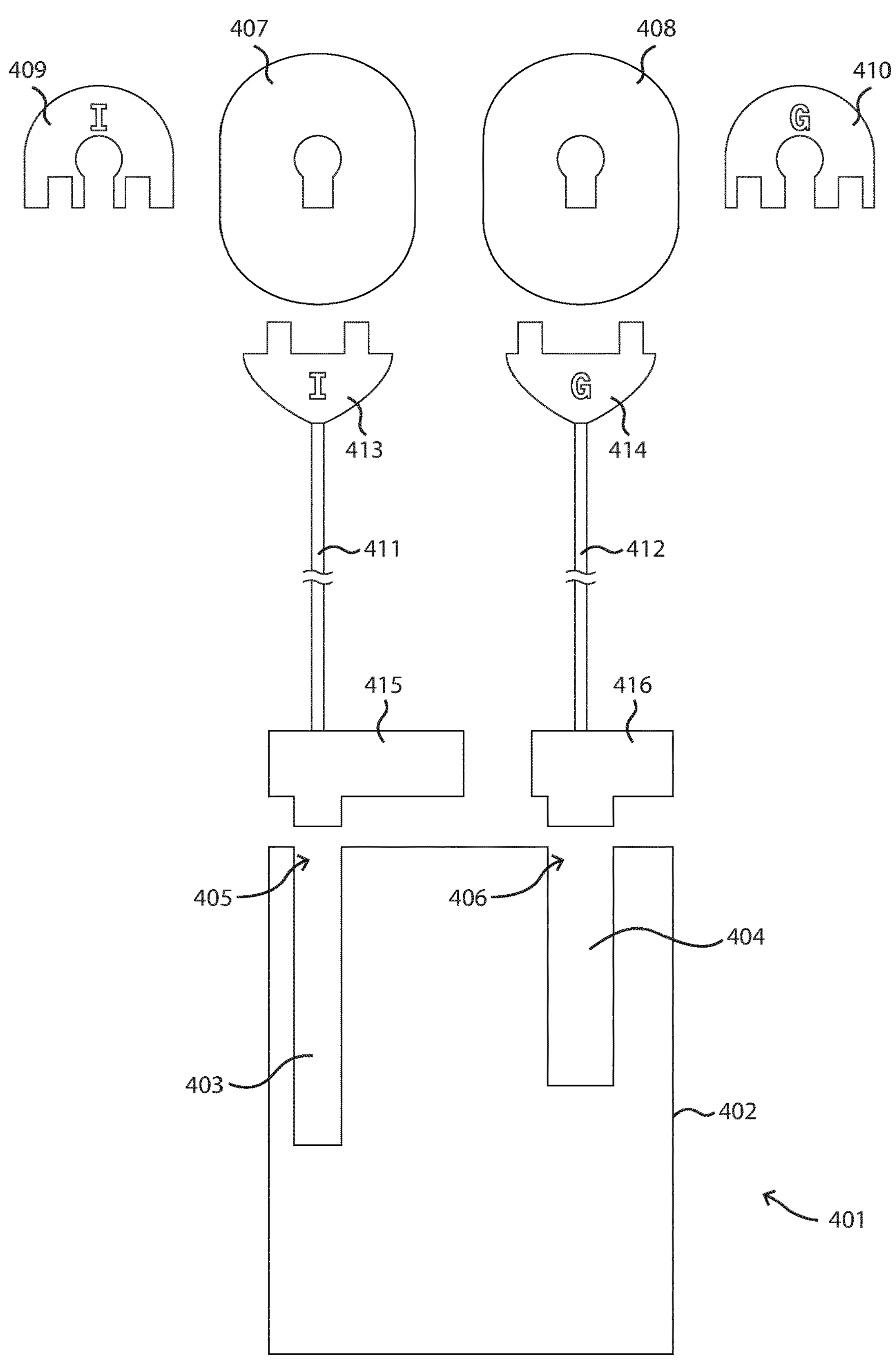
Figure 7B:
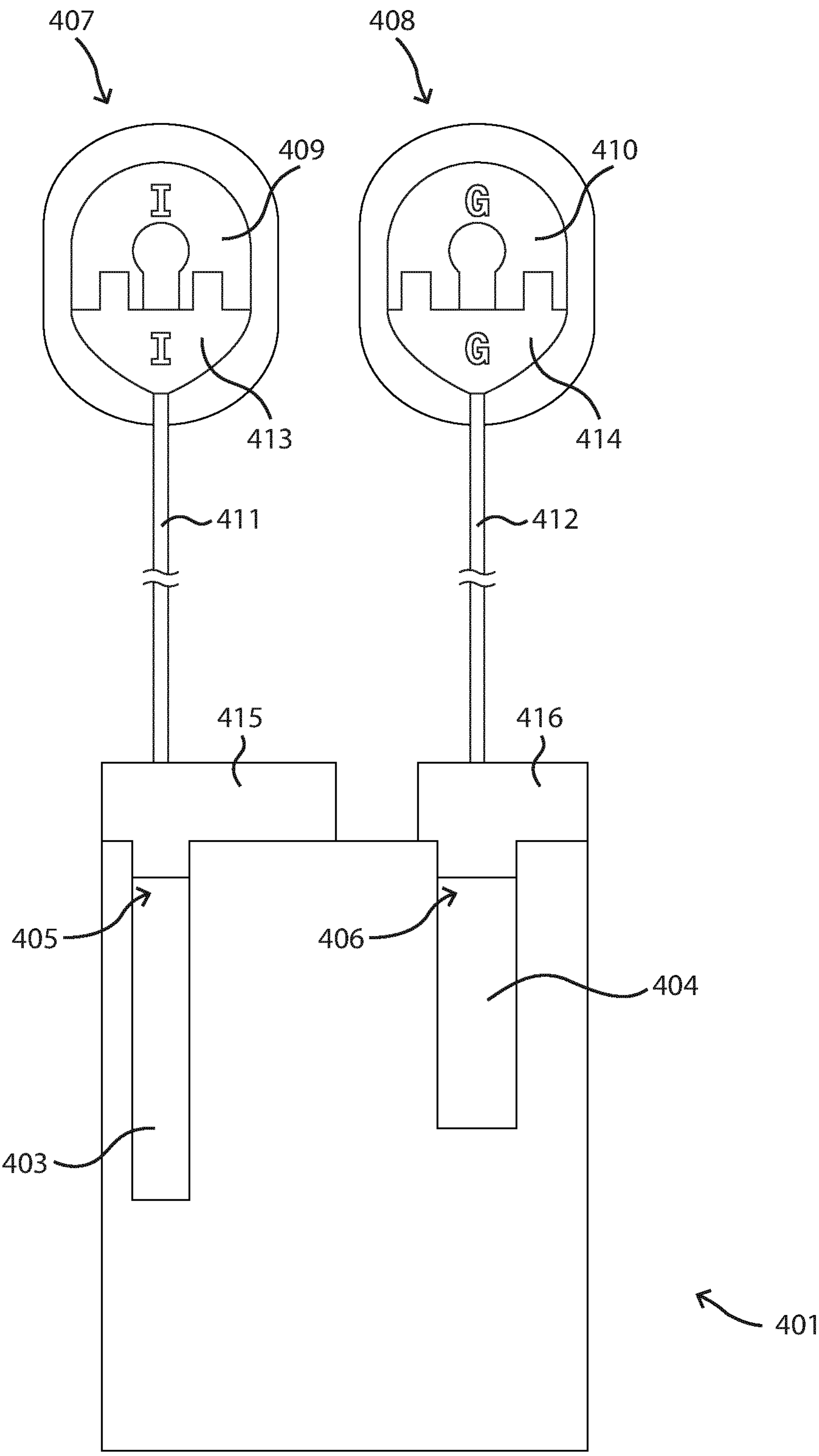

The invention(s) will be further explained with respect to figures, wherein:

FIGS. 1*a* and 1*b* schematically show a first embodiment of the system according to the invention, wherein FIG. 1*a* shows the infusion element and transport element in a disconnected state and FIG. 1*b* shows the infusion element and transport element in a connected state;

FIGS. 2*a* and 2*b* schematically show a second embodiment of the system according to the invention, wherein FIG. 2*a* shows the infusion element and transport element in a disconnected state and FIG. 2*b* shows the infusion element and transport element in a connected state;

FIGS. 3*a* and 3*b* schematically show a third embodiment of the system according to the invention, wherein FIG. 3*a* shows a front view and FIG. 3*b* a top view;

FIGS. 4*a* and 4*b* schematically show a fourth embodiment of the system according to the invention, wherein FIG. 4*a* shows the infusion element and transport element in a disconnected state and FIG. 4*b* shows the infusion element and transport element in a connected state;

FIGS. 5*a*-5*f* show the adjustment of the infusion element of the fourth embodiment of FIGS. 4*a* and 4*b* in more detail, wherein FIGS. 5*a*-5*c* show atop view of the first infusion set and FIGS. 5*d*-5*f* show a cross section through a main plane of the first infusion set;

FIGS. 6*a* and 6*b* show a perspective view of an infusion element and two transport elements of the fourth embodiment;

FIGS. 7*a* and 7*b* schematically show a fifth embodiment of the system according to the invention, wherein FIG. 7*a* shows the infusion element and transport element in a disconnected state and FIG. 7*b* shows the infusion element and transport element in a connected state In the figures same or similar features are referred to by same reference numerals, increased by one hundred (100), two hundred (200) and three hundred (300) for the second, third and fourth embodiment, respectively.

For the sake of clarity and/or simplicity features that may be relevant for understanding the invention are shown in the figures, even though such features might not normally be visible in the views as shown. Further, some features of the system may not be shown for the sake of simplicity. The features that are shown may be shown in a simplified and/or enlarged way and/or in any other way different from reality but improving the readability of the figures.

FIGS. 1*a* and 1*b* show a schematic front view of a system 1 for regulating the concentration of glucose in the blood of a person in two different conditions and/or states, as will be described below. Said system 1 comprises a device 2 for in this embodiment selectively supplying two substances, i.e. insulin and glucagon. Said device 2 comprises in this embodiment two receiving spaces 3, 4 for receiving and accommodating respective reservoirs containing said substances. As is shown in FIGS. 1*a* and 1*b*, in this embodiment the receiving spaces 3, 4 each have a different length and diameter, wherein the length and diameter are adapted to the type of reservoir to be received therein, such that each receiving space 3, 4 is able to receive only one type of reservoir. In particular, in this embodiment the receiving space 3 is able to receive an insulin reservoir and the receiving space 4 is able to receive a glucagon reservoir, which glucagon reservoir is shorter and thicker as compared to the insulin reservoir. The device 2 further comprises ports 5, 6, via which ports 5, 6 a respective reservoir may be inserted into the respective receiving space 3, 4 and to which an infusion set can be connected. The ports 5, 6 are in this embodiment identical in size and shape.

FIGS. 1*a*, 1*b* further show two infusion sets, wherein each infusion set comprises an infusion element 7, 8 comprising an infusion means for infusing a said substance into the body of said person, said infusion means for example being a cannula, catheter, needle, or nozzle, and said infusion means comprising an inlet end for receiving said substance and an outlet end for infusing said substance into said body. Such an infusion means is provided at the back of the infusion element 7, 8 as shown in FIGS. 1*a*, 1*b* and therefore not visible in FIGS. 1*a*, 1*b*. However, such an infusion element is well known to the skilled person and thus the skilled person would understand how to embody such an infusion means. The infusion elements 7, 8 further each comprise a respective first connector 9, 10.

In this embodiment each infusion set further comprises a respective tube 11, 12 as transport means that is part of a transport element. At an outlet end of the tubes 11, 12 each tube 11, 12 comprises a second connector 13, 14 that is connectable to a said first connector 9, 10 of a said infusion element 7, 8 such that in a connected condition as shown in FIG. 1*b* in which the second connectors 13, 14 are connected to the first connectors 9, 10 a medium through flow connection is provided between the outlet end of the tubes 11, 12 and the inlet end of the infusion means for feeding the substance to the infusion means. At an inlet end of the tubes 11, 12, which is located at the other end of the tubes 11, 12, said tubes comprise a respective third connector 15, 16 for connecting to a said port 5, 6 such that in a connected condition as shown in FIG. 1*b* in which a said third connector 15, 16 is connected to a said port 5, 6 a medium through flow connection is provided between a said reservoir contained in a said receiving space 3, 4 and the inlet end of the tubes 11, 12 for receiving a said substance from a said reservoir. In the connected condition of FIG. 1*b* wherein the third connectors 15, 16 are connected to respective ports 5, 6 and the second connectors 13, 14 are connected to respective first connectors 9, 10 it is thus possible to feed a said substance to said person via a said tube 11, 12 and a said infusion element 7, 8.

Said device 2 further comprises a controller 17 for controlling said device 2 such that a certain amount of a said substance is supplied and thereby infused into the body of the person via a respective infusion set.

As will be clear from FIGS. 1*a*, 1*b*, the first connectors 9, 10, second connectors 13, 14, third connectors 15, 16 and ports 5, 6 are in this embodiment mechanically substantially the same. Therefore it is possible to connect any first connector 9, 10 to any second connector 13, 14 and to connect any third connector 15, 16 to any port 5, 6. This makes the system 1 mechanically relatively simple and/or cheap to manufacture, but it can give risks when the tubes 11, 12 are connected to the wrong port 5, 6, especially if said tube has already been in use and is thus already filled with the other substance, or when the infusion elements 7, 8 are connected to the wrong tube 11, 12. Therefore a mischanneling prevention system is provided, wherein in this embodiment the device 2 is arranged such that the device 2 will only supply a said substance for feeding the substance to the person if the tubes 11, 12 are connected to the correct port 5, 6 and, after adjusting the infusion elements 7, 8, the correct infusion element 7, 8. In the embodiment of FIGS. 1*a*, 1*b* the mischanneling prevention system is electronical. The controller 17 has two electrical or electronical circuits 18, 19, wherein each circuit 18, 19 comprises a respective electromagnetic coil 20, 21. The transport elements each have a respective electronical circuit 22, 23 comprising respective wires that extend along the tubes 11, 12 from and including the respective second connectors 13, 14 and third connectors 15, 16, wherein each circuit 22, 23 comprises a respective electromagnetic coil 24, 25 in the respective third connector 15, 16 and a respective electromagnetic coil 26, 27 in the respective second connector 13, 14. The infusion elements 7, 8 and in particular the respective first connectors 9, 10 thereof each have a respective electronical circuit 28, 29, each circuit 28, 29 comprising a respective coil 30, 31. In the connected condition of FIG. 1*b* the coils 20, 21 are located adjacent the coils 24, 25, and the coils 26, 27 are located adjacent the coils 30, 31 such that communication between the various electronical circuits 18, 22, 28, and 19, 23, 29 can take place via the coils. Each circuit of the infusion elements 7, 8 has a respective first memory, embodied here as first chip 34, 35 and in this case provided as part of the respective first connectors 9, 10, and each circuit 22, 23 of the transport elements has a respective second memory, embodied here as second chip 32, 33 and in this case provided as part of the respective second connectors 13, 14. In particular the chips 32-35 are in this embodiment provided as integral parts of the transport elements and infusion elements, respectively.

The second chips 32, 33 of the transport elements may be pre-set, i.e. pre-written with information indicative of the type of substance to be infused with that infusion set, and the first chips 34, 35 may be writable chips, i.e. said first chips 34, 35 are provided as adjustable elements. The controller 17 can check if the correct transport element is connected to the correct port 5, 6 by reading the information of the second chips 32, 33 and checking if that information is read, i.e. received, via the correct electronical circuit 18, 19. The information stored in the second chips 32, 33 will be used for writing the first chips 34, 35 of the infusion elements 7, 8. Prior to storing this information in the first chips 34, 35 the infusion elements 7, 8 are thus neutral and can be used for either substance. After writing the information in the first chips 7, 8 the infusion elements 7, 8 are adapted to the type of transport element connected thereto and thereby adjusted to either insulin or glucagon, i.e. to the first or second condition. After adjusting the infusion elements the controller 17 can further check if the correct infusion element 7, 8 is connected to the transport element by reading the information of the first chips 34, 35 and checking if that information is also read, i.e. received, via the correct electronical circuit 18, 19, wherein communication between the controller 17 and the first chips 34, 35 takes place via the circuits 22, 23 of the transport elements.

Alternatively the second chips may be pre-set, i.e. prewritten with information, but said information may not yet be indicative of the type of substance. For example, each chip may comprise unique information, such as a unique number, and upon the first use of the infusion sets the controller 17 may be arranged to allocate said unique information to the type of substance based on via which port said information is received. In further use of the infusion sets the mischannelling can be detected based on this unique and now allocated information. This alternative variant provides the advantage that prior to their first use also the transport elements can be used for either substance.

Alternatively also the second chips may be writable chips. The controller 17 can write the second chips 32, 33 with information indicative of the type of substance and then the respective first chips 34, 35 can be written based on the information of the second chips 32, 33. Writing said chips directly or indirectly via the controller 17 with said information takes place via the circuits 18, 19, 22, 23, 28, 29 and by knowing to which port 5, 6 the circuits 18, 19 are related. Writing said chips 32, 33, 34, 35 may take place at the first use of a new infusion set. After writing the chips 32, 33, 34, 35 it may not be possible to overwrite the chips, such that after the first use the infusion sets cannot be used for the other substance. After writing the chips the controller 17 can check if the correct transport element is connected to the correct port 5, 6 by reading the information of the second chips 32, 33 and checking if that information is read, i.e. received, via the correct electronical circuit 18, 19. The controller 17 can further check if the correct infusion element 7, 8 is connected to the correct transport element by reading the information of the first chips 34, 35 and checking if that information is also read, i.e. received, via the correct circuit 18, 19, wherein communication between the controller 17 and the first chips 34, 35 takes place via the circuits 22, 23 of the transport elements. This alternative variant provides the advantage that prior to their first use both the transport element and the infusion elements are neutral and can thus be used for either substance, and after adjusting the transport elements and infusion elements these can only be used for the correct substance.

It the controller 17 has detected that the correct transport elements are connected to the correct ports 5,6 and the correct infusion elements 7, 8 are connected to the correct transport elements, said controller 17 may be arranged to supply a said substance in accordance with a normal use of the device, for example upon request by a user inputting to supply a dose or in accordance with an algorithm calculating the amount of substance to be dosed. If the controller 17 has detected that the transport elements are connected to the wrong ports 5,6 and/or the infusion elements 7, 8 are connected to the wrong transport elements or any of these are not connected at all, said controller 17 is arranged to not supply a said substance and/or to provide a warning signal.

In this embodiment all circuits may be powered via the device 2.

FIGS. 2*a*, 2*b* show a second embodiment of the system 101. Only the differences with the first embodiment of FIGS. 1*a* and 1*b* will be described here. For a further description of the second embodiment of FIGS. 2*a*, 2*b* the reader is referred to the description of FIGS. 1*a* and 1*b*.

The second embodiment of the system 101 of FIGS. 2*a*, 2*b* differs in that the infusion elements 107, 108 communicate via a respective transmitter 140, 141 with the controller 117 and not via the tubes 111, 112. The transmitters 140, 141 are provided as separate elements that can be releasably connected to the infusion elements 107, 108 and thereby reused for new infusion sets. Each transmitter 140, 141 comprises a respective electrical or electronical circuit 128, 129 which comprise a respective coil 130, 131 and respective first chip 134, 135. A further difference is thus that the first chips 134, 135 are provided as part of separate elements, i.e. transmitters 140, 141 that are separate from the infusion elements and can be, in this embodiment, releasably connected to the infusion elements 107, 108. The first chips 134, 135 are in this embodiment thus not an integral part of the infusion elements 107, 108.

A further difference of this embodiment is that the transport elements each comprise two second chips 132*a*, 132*b*, respectively, and 133*a*, 133*b* respectively. The first second chips 132*a*, 133*a* are comprised in circuits 122*a*, 123*a* of the second connectors 113, 114 of the transport elements, and the second second chips 132*b*, 133*b* are comprised in circuits 122*b*, 123*b* of the third connectors 115, 116 of the transport elements. The information of the first second chips 132*a*, 133*a* of the transport elements can be exchanged with the circuits 128, 129 of the transmitters 140, 141 that are connected to the infusion elements 107, 108 via coil pairs 130, 126 and 131, 127, similar as described with respect to the first embodiment of FIGS. 1*a*, 1*b*. The information of the second second chips 132*b*, 133*b* can be exchanged with the device 102 via respective coil pairs 124, 120 and 125, 121. The controller 117 is thus arranged to receive the information of the second second chips 132*b*, 133*b* via said respective coils 124, 125 and is thereby able to detect if the third connectors 115, 116 are connected to the correct port 105, 106 and thereby if the transport elements are connected to the correct port. Because the controller 117 receives the information of chip pairs 132*a*, 134, and of chip pairs 133*a*, 129 the controller 117 is able to detect if the infusion element is connected to the correct transport element, at least after adjusting the infusion elements 107, 108.

Similar to the first embodiment the second chips 132*a*, 132*b*, 133*a*, 133*b* of the transport elements may be pre-set, i.e. pre-written with information indicative of the type of substance to be infused with that infusion set or may comprise information that can be allocated to the type of substance at first use. The information stored in the first second chips 132*a*, 133*a* is preferably the same or similar to the information stored in second second chips 132*b*, 133*b*, such that it is clear which first and second second chips belong to the same transport element.

Adjusting the infusion elements 107, 108 to their first or second condition may be arranged in various ways.

As a first example the information written in the first chips 134, 135 is pre-set, i.e. the first chips 134, 135 are pre-written with information indicative of the type of substance to be infused with that infusion element or with information that can be allocated to the type of substance at the first use of the infusion sets. By providing the first chips 134, 135 as part of the transmitters 140, 141, respectively and thereby as separate adjusting elements, the infusion elements 107, 108 may easily be adjusted by connecting a respective transmitter 107, 108 thereto. Prior to connecting the transmitters 140, 141 to the infusion elements 107, 108 the infusion elements 107, 108 are thus neutral and can be used for either substance. The information transmitted by the transmitters 140, 141 will be a combination of the information of the first chips 134, 135 and first second chips 132*a*, 133*a* as described above, and thereby the controller 117 is able to detect if the correct infusion element 107, 108 is connected to the correct transport element.

Alternatively the first chips 134, 135 may be writable chips and thus provided as adjustable elements that are separate from the infusion elements and releasably connectable thereto. Writing and thereby adjusting the first chips 134, 135 may take place similarly as described with respect to the first embodiment, i.e. based on information of the second chips and in this case the first second chips 132*a*, 133*a*, respectively. Prior to storing this information in the first chips 134, 135 the infusion elements 107, 108 are thus neutral and can be used for either substance. After writing the information in the first chips 107, 108 the infusion elements 107, 108 are adapted to the type of transport element connected thereto and thereby adjusted to either insulin or glucagon, i.e. to the first or second condition. As described above, the controller 117 is able to check if the correct transport element is connected to the correct port based on second second chips 132*b*, 133*b* and if the correct infusion element 107, 108 is connected to the correct transport element based on the information transmitted by respective transmitters 140, 141, which is a combination of the information of the first chips 134, 135 and first second chips 132*a*, 133*a* as described above.

In this embodiment the transmitters 140, 141 comprise a battery or other power source for powering the transmitter, but also the circuits 122*a*, 123*a* of the second connectors 113, 114 respectively.

For receiving the information from the transmitters 140, 141 said controller 117 comprises a receiving means, which is schematically illustrated by means of waves 148.

It is noted that the transmitters 140, 141 are shown as separate elements. Alternatively these can be an integral part of the infusion elements 107, 108, in which case the first chips 134, 135 are writable chips. Alternatively the transmitters 140, 141 can be part of a glucose sensor element (not shown) and may be located near the infusion elements 107, 108. In such a case it is preferred that the infusion elements 107, 108 comprise their own circuits comprising a said first chip and two coils, and the transmitters 140, 141 may comprise further circuits comprising a third chip and coil, such that via the coil of the transmitter 140, 141 and one of the coils of the infusion elements 107, 108 the circuits of the infusion elements 107, 108 and transmitters 140, 141 are able to communicate with each other, and the infusion elements 107, 108 are able to communicate with the second connectors 113, 114 of the transport elements via the other coil of the infusion element and the coil of the circuit of the second connector 113, 114 as described with respect to FIGS. 1*a*, 1*b*. Said two coils of the infusion elements 107, 108 may alternatively be provided as one coil, as will be clear for the skilled person.

FIGS. 3*a* and 3*b* show a third embodiment of the system 201. Only the differences with the second embodiment of FIGS. 2*a* and 2*b* will be described here. For a further description of the third embodiment of FIGS. 3*a*, 3*b* the reader is referred to the description of FIGS. 2*a* and 2*b*.

The third embodiment of the system 201 of FIGS. 3*a* and 3*b* differs from the second embodiment in that the second chips 232*a*, 232*b*, 233*a*, 233*b* may be writable chips and thereby adjustable. At the first use of the transport elements the second connectors 213, 214 may be connected or at least in contact with the third connectors 215, 216 which are in turn connected to the ports 205, 206, as is shown in FIG. 3*a* with respect to the transport element shown on the right, i.e. the transport element connected to port 206. As is clear from FIG. 3*a*, the third connectors 215, 216 comprise a circuit 222*b*, 223*b* respectively that comprises two coils 224*a*, 224*b* and 225*a*, 225*b* respectively. Via coil pairs 224*a*, 220 and 225*a*, 221 the device 202 and in particular the controller 217 is able to communicate with the third connectors 215, 216 respectively. In this embodiment the third connectors 215, 216 are able to communicate with second connectors 213, 214 respectively via coil pairs 224*b*, 226 and 225*b*, 227, but this may be arranged in other suitable ways as will be clear for the skilled person. Based on to which port 205, 206 the transport elements are connected the controller 217 is able to write information indicative of the type of substance in the chips 232*b*, 232*a* of the first transport element and in the chips 233*b*, 233*a* of the other transport element, i.e. the information that will be written in chip 232*b*, 232*a* will be indicative of insulin because the third connector 215 connects to the insulin port 205 and the information that will be written in chip 232*b*, 232*a* will be indicative of glucagon because the third connector 216 connects to the glucagon port 206. After adjusting the transport elements to one type of substance only mischanneling can be prevented. An advantage of providing adjustable transport elements is that these are neutral prior to their first use as well and can thus be used for either insulin or glucagon prior to being adjusted.

The infusion elements are not shown in FIGS. 3*a*, 3*b* but may be similar to the second embodiment of the system as shown in FIGS. 2*a*, 2*b* and may function as described above with respect to FIGS. 2*a*, 2*b*.

It is noted that even though some elements are disclosed to comprise a circuit comprising two coils, only one coil may be provided where applicable. This will be clear for the skilled person.

FIGS. 4*a* and 4*b* show a fourth embodiment of the system 301. Only the differences with the first embodiment of FIGS. 1*a* and 1*b* will be described here. For a further description of the fourth embodiment of FIGS. 4*a*, 4*b* the reader is referred to the description of FIGS. 1*a* and 1*b*. Parts of the system 301 according to the fourth embodiment of FIGS. 4*a*, 4*b* are shown in further detail in FIGS. 5*a*-5*f* and in a perspective view in FIGS. 6*a*, 6*b*.

The fourth embodiment of FIGS. 4*a*, 4*b* and FIGS. 5*a*-5*f* show a mechanical embodiment of adjusting the infusion elements 307, 308.

As is clear from FIGS. 4*a*, 4*b*, the ports 305, 306 of the device 302 are different in size and the third connectors 315, 316 have a connecting part that is also different in size and in particular adapted to the size of the ports 305, 306 respectively, such that the third connectors 315, 316 of the two infusion sets can physically only connect to one of the ports 305, 306 of the device 302, i.e. the third connector 315 can only connect to port 305 and third connector 316 can only connect to port 306. As a result thereof, the transport elements of the infusion sets are adapted to one type of substance only, i.e. the first transport element comprising second connector 313 and third connector 315 is adapted to insulin, as is indicated by the "I" on the second connector 313, and the second transport element comprising second connector 314 and third connector 316 is adapted to glucagon, as is indicated by the "G" on the second connector 314.

In accordance with the invention, the infusion elements 307, 308 are in a neutral condition prior to connecting to the transport elements, as is shown in FIG. 4*a*, i.e. the infusion elements 307, 308 can be connected to and/or function with either one of the two transport elements. Upon connecting the second connectors 313, 314 of the transport elements to the first connectors 309, 310 of the infusion elements 307, 308 respectively the infusion elements and in particular the first connectors thereof are adjusted from said neutral condition to a first or second condition, wherein in the first or second condition the infusion element is adapted to a first or second type of transport element only. As is shown in FIG. 1*b*, after adjusting the infusion elements 307, 308 the first infusion element 307 is adapted to the insulin transport element comprising the second connector 313 and the second infusion element 308 is adapted to the glucagon transport element comprising the other second connector 314. The second connectors 313, 314 comprise a respective adjusting element 350, 351 for adjusting the infusion elements 307, 308. Adjusting the infusion elements 307, 308 using the adjusting elements 350, 351 will be described in more detail with respect to FIGS. 5*a*-5*f*, which show the adjustment of the first infusion element 307 using the first transport element having adjusting element 350 in more detail.

FIGS. 5*a*-5*f* show that the second connector 313 of the transport element comprises said adjusting element 350, which is in this embodiment a protrusion located at the end of one of two legs of the second connector 313. Adjusting the infusion element 307 is best illustrated with respect to FIGS. 5*d*-5*f* which show a simplified cross sectional view through the infusion element 307. This view shows that in the condition of FIG. 5*d* the infusion element 307 is neutral, i.e. not adapted to either insulin or glucagon. Upon connecting the second connector 313 to the first connector 309 of the infusion element 307, a moveable element 352 of the infusion element is moved by the adjusting element 350. In this embodiment the moveable element 352 is an adjustable element of the infusion element 307. The moveable 352 is in this particular embodiment rotated by the adjusting element 350 and can therefore alternatively be referred to as a rotatable element. The moveable element 352 comprises two fingers 353 that in this embodiment extend substantially outwardly and are in this embodiment located at substantially opposing sides of the moveable element 352. The infusion element 307 further comprises two locking protrusions 354 that in this embodiment extend substantially inwardly in the direction of the moveable element 352. As is shown in FIG. 5*e*, as a result of rotating the moveable element 352 one of the fingers 353 is moved beyond one of the locking protrusions 354. The shape of the fingers 353 and/or locking protrusions are chosen such that the fingers 353 can be moved beyond the locking protrusion when moved, i.e. rotated, in a first direction upon connecting the second connector 313 to the first connector 309, but not moved back beyond the locking protrusion when moved, i.e. rotated, in a second, opposing direction. FIG. 5*f* shows that even after disconnecting the second connector 313 from the first connector 309 the moveable element 352 remains in its locked position in which the finger 353 is locked by the locking protrusion 354, such that it is now only possible to connect an insulin second connector 313 to the first connector 309. It is thus not possible anymore to connect the other second connector 314 to the first connector 309. In the position shown in FIGS. 5*e* and 5*f* the infusion element 307 is thereby adjusted to one type of transport element and thereby one type of substance only, in this case insulin which is also indicated by the "I" that is now visible in a window 355, see FIGS. 5*a*-5*c*. As is clear from FIGS. 5*d*-5*f* the moveable element 352 has both an "I" for insulin and "G" for glucagon and dependent on the direction of movement either the "I" as shown in FIGS. 5*b*, 5*c*, 5*e*, 5*f* is visible in the window 355 or the "G". As is shown in FIG. 4*a*, the glucagon second connector 314 of the other transport element has its adjusting element 351 located on the other leg of the second connector 314. If such a second connector 314 is connected to a neutral, i.e. not yet adjusted, infusion element 307, 308 the moveable element 352 is moved, i.e. rotated, in the opposite direction as shown in FIGS. 5*a*-5*f* and the other finger 353 of the two fingers 353 is locked by the other locking protrusion 354 of the two locking protrusions 354, such that it is then adapted to glucagon second connectors 314.

FIGS. 6*a*, 6*b* show an infusion element 307 in its neutral condition to which a second connector 313, 314 can be connected. From these figures it is clear that the second connectors 313, 314 can be connected to the first connector 309 of the infusion element 307 in only one orientation thereof. This is, in this embodiment, the result of longitudinal guiding ribs 356 of the infusion element 307 which can be accommodated in longitudinal recesses 357 of the second connectors 313, 314 when connecting a said second connector 313, 314 to the infusion element 307, but this can be achieved in any other suitable way. Because it is not possible to connect the second connectors 313, 314 in an opposite orientation, the adjusting elements 350, 351, respectively, thereof are always at the same side, i.e. the right or left side, respectively, in the perspective view of FIG. 6*b*, when connecting to the first connector 309. As a result of said second connector 313, 314 being able to connect to the first connector 309 in one orientation only it is thus made sure that the infusion element 307 is adjusted correctly by moving the adjustable element 352 thereof in the correct direction for that second connector 313, 314.

It is noted that in the fourth embodiment of FIGS. 4*a*-6*b* no controller is shown. Said device 302 does have a controller for controlling the device 302, but because it is an mechanical adjustment embodiment the controller is not required for adjusting the infusion element and/or for checking correct channeling of the infusion sets.

It is further noted that in the fourth embodiment of FIGS. 4*a*-6*b* the transport element is suitable for transporting one type of substance only, i.e. the transport element is not adjustable. It can be foreseen that for example in a way similar as shown in FIGS. 3*a* and 3*b* the transport element can be adjustable as well by means of the ports of the device comprising a second adjusting element for adjusting a second adjustable element of the third connector of the transport element, wherein the third connector adjusts the adjusting element of the second connector of the transport element such that after adjusting the adjusting element of the second connector the second connector is able to adjust the adjustable element of the infusion element.

FIGS. 7*a* and 7*b* show a fifth embodiment of the system 401. Only the differences with the fourth embodiment of FIGS. 4*a*-6*b* will be described here. For a further description of the fifth embodiment of FIGS. 7*a*, 7*b* the reader is referred to the description of FIGS. 4*a*-6*b*.

FIGS. 7*a* and 7*b* show an alternative mechanical embodiment for adjusting the infusion element 407, 408. The embodiment of FIGS. 7*a* and 7*b* is mechanically simple, wherein the first connectors 409, 410 are provided as separate elements that are, optionally releasably, connectable to the infusion elements 407, 408. The first connectors 409, 410 are adapted to one type of transport element only, so after connecting the first connectors 409, 410 to a respective infusion element 407, 408 the infusion elements 407, 408 are adapted to one type of transport element only. In this embodiment the first connectors 409, 410 thus function as separate adjustable elements that once connected to the infusion elements 407, 408 connect the respective infusion element 407, 408 to a first or second condition, respectively. In the fifth embodiment of FIGS. 7*a* and 7*b* the first connectors 409, 410 are adapted to one type of transport element only by means of the first connectors 409, 410 having a different shape and the shapes of the second connectors 413, 414 being adapted thereto. The second connector 313 can therefore only connect to first connector 409 and the other second connector 314 can only connect to the other first connector 410.

It is noted that the invention is not limited to the shown embodiments but also extends to variants within the scope of the appended claims.

The invention claimed is:

1. An infusion set for a system for regulating the concentration of glucose in the blood of a person, said infusion set comprising:

an infusion element comprising an infusion member for infusing a substance into a body of said person, said infusion member means comprising an inlet end for receiving said substance and an outlet end for infusing said substance into said body, wherein said infusion element comprises a first connector for connecting to a second connector of a transport element of the infusion set, and said transport element comprising a transport member, the second connector being arranged at an outlet end of the transport member that is connectable to said first connector of said infusion element such that in a connected condition in which the second connector of the transport element is connected to the first connector of the infusion element a medium through flow connection is provided between the outlet end of the transport member and the inlet end of the infusion member for feeding the substance to the infusion member, wherein said infusion element is adjustable from a neutral condition to a first or second condition, wherein in the first or second condition the infusion element is adapted to a first or second type of transport element only.

2. The infusion set according to claim 1, wherein the infusion set comprises at least one adjustable interface configured to transition the infusion element from its neutral condition to either its first or second condition.

3. The infusion set according to claim 2, wherein the infusion element is mechanically adjustable such that adjusting the infusion element comprises moving the at least one adjustable interface from a neutral position in accordance with the neutral condition to either a first or second position in accordance with the first or second condition, respectively.

4. The infusion set according to claim 1, wherein the infusion set comprises at least one adjusting interface configured to adjust the infusion element from its neutral condition to either its first or second condition.

5. The infusion set according to claim 4, wherein said transport element comprises said at least one adjusting interface configured to adjust the infusion element from its neutral condition to either its first or second condition when the second connector thereof is connected to the first connector.

6. The infusion set according to claim 4, wherein the at least one adjusting interface is either a first adjusting interface configured to adjust the infusion element from its neutral condition to its first condition or a second adjusting interface configured to adjust the infusion element from its neutral condition to its second condition, wherein the first adjusting interface is different from the second adjusting interface.

7. The infusion set according to claim 6, wherein the first adjusting interface has at least partly a different shape than the second adjusting interface and/or is located at a different position and/or in a different orientation on the transport member.

8. The infusion set according to claim 1, wherein the infusion element is electronically adjustable.

9. The infusion set according to claim 1, wherein at least the first and second conditions are or comprise different indicators for indicating the first or second condition, respectively, of the infusion element.

10. The infusion set according to claim 1, wherein said infusion element cannot be adjusted from its first or second condition back to its neutral condition.

11. A system for regulating the concentration of glucose in the blood of a person, said system comprising:

at least two infusion sets according to claim 1;

a device for selectively supplying at least two substances contained in respective reservoirs, said device comprising:

at least two receiving spaces for accommodating a respective reservoir, at least two ports for connecting to a respective transport element, and a controller for controlling said device such that a certain amount of said substance is supplied and thereby infused into the body of the person, wherein an inlet end of each of the transport elements is connectable to a respective port of said device.

12. The system according to claim 11, wherein each transport element of the at least two infusion sets is adapted to only one port out of the at least two ports of the device.

13. The system according to claim 11, wherein the transport elements of the at least two infusion sets are adjustable from a neutral condition to a first or second condition, and wherein in the first or second condition each transport element is adapted to a first or second port, respectively, and wherein the device is arranged for adjusting the transport element to its first or second condition.

14. The system according to claim 13, wherein the transport element of each of the at least two infusion sets comprises at least one adjusting interface for adjusting the respective infusion element from its neutral condition to either its first or second condition when the second connector thereof is connected to the first connector;

wherein upon adjusting each transport element to its first or second condition the adjusting interface of the respective transport element is able to adjust the respective infusion element from its neutral condition to either its first or second condition and/or the respective infusion element is adjusted from its neutral condition to either its first or second condition.

15. A use of the system according to claim 11, comprising the steps, to be performed in any suitable order, of:

a) providing the system;

b) connecting the inlet end of a first transport element of a first infusion set of the at least two infusion sets to a first port of said device and the inlet end of a second transport element of a second infusion set of the at least two infusion sets to a second port of said device;

c) adjusting a first infusion element of the first infusion set from a neutral condition to a first condition and a second infusion element of the second infusion set from a neutral condition to a second condition;

d) connecting a second connector of the first transport element to a first connector of the first infusion element and a second connector of the second transport element to a first connector of the second infusion element.

16. The use according to claim 15, wherein step c) is performed by performing step d).

* * * * *